(12) United States Patent
Woodard et al.

(10) Patent No.: US 12,207,830 B2
(45) Date of Patent: *Jan. 28, 2025

(54) CHEVRON OSTEOTOMY TOOLS AND METHODS

(71) Applicant: WRIGHT MEDICAL TECHNOLOGY, INC., Memphis, TN (US)

(72) Inventors: Joseph Ryan Woodard, Memphis, TN (US); Daniel E. Free, Arlington, TN (US); Brian Thoren, Memphis, TN (US); Jason Edie, Sandy, UT (US); Andy Leither, Akron, OH (US); David Kay, Akron, OH (US); Anthony Perera, Cardiff (GB); Bryan Denhartog, St. Paul, MN (US); David Redfern, Hove (GB); Joel Vernois, Picquigny (FR)

(73) Assignee: WRIGHT MEDICAL TECHNOLOGY, INC., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/582,755

(22) Filed: Feb. 21, 2024

(65) Prior Publication Data

US 2024/0245413 A1    Jul. 25, 2024

Related U.S. Application Data

(62) Division of application No. 18/047,717, filed on Oct. 19, 2022, now Pat. No. 11,937,833, which is a
(Continued)

(51) Int. Cl.
A61B 17/17    (2006.01)
A61B 17/02    (2006.01)

(52) U.S. Cl.
CPC ........ *A61B 17/1775* (2016.11); *A61B 17/025* (2013.01); *A61B 17/1735* (2013.01)

(58) Field of Classification Search
CPC ..... A61B 17/17; A61B 17/1775; A61B 17/15; A61B 17/151; A61B 17/152
See application file for complete search history.

(56) References Cited

U.S. PATENT DOCUMENTS

| | | |
|---|---|---|
| 4,421,112 A | 12/1983 | Mains et al. |
| 6,358,250 B1 | 3/2002 | Orbay |

(Continued)

FOREIGN PATENT DOCUMENTS

| | | |
|---|---|---|
| CN | 204049714 U | 12/2014 |
| DE | 201010948 U1 | 9/2001 |

(Continued)

OTHER PUBLICATIONS

First Examination Report issued in connection with corresponding Australian Patent Application No. 201631799, Jun. 15, 2018, 6 pages.
(Continued)

*Primary Examiner* — Si Ming Ku
(74) *Attorney, Agent, or Firm* — DUANE MORRIS LLP

(57) ABSTRACT

A system and method for use when forming an osteotomy that rely upon an arrangement of surgical instruments with a targeting guide having a handle extending substantially along a longitudinal axis, with one or more burr holes extending from a first side of the handle to a second side of the handle. A head is coupled to a distal end of the longitudinal handle. The head defines a plurality of guide holes sized and configured to receive a k-wire therethrough. The arrangement allows accurate adjustment of the surgical instruments in relation to the bones targeted for the osteotomy.

15 Claims, 31 Drawing Sheets

Related U.S. Application Data division of application No. 15/756,446, filed as application No. PCT/US2016/049981 on Sep. 1, 2016, now Pat. No. 11,504,139.

(60) Provisional application No. 62/213,161, filed on Sep. 2, 2015.

(56) References Cited

U.S. PATENT DOCUMENTS

| | | | |
|---|---|---|---|
| 6,695,847 | B2 | 2/2004 | Bianchetti et al. |
| D549,331 | S | 8/2007 | Tomatsu et al. |
| 2008/0262500 | A1* | 10/2008 | Collazo .............. A61B 17/8095 606/88 |
| 2009/0099571 | A1 | 4/2009 | Cresina et al. |
| 2009/0204148 | A1 | 8/2009 | Lenke et al. |
| 2011/0106086 | A1 | 5/2011 | Laird |
| 2012/0130383 | A1 | 5/2012 | Budoff |
| 2013/0090662 | A1 | 4/2013 | Hanson et al. |
| 2014/0180348 | A1 | 6/2014 | Thoren et al. |
| 2014/0194999 | A1 | 7/2014 | Orbay et al. |
| 2014/0276843 | A1 | 9/2014 | Koay et al. |
| 2015/0071885 | A1 | 3/2015 | Saw et al. |
| 2015/0230822 | A1 | 8/2015 | Hanson et al. |
| 2016/0367270 | A1* | 12/2016 | Garlock ............. A61B 17/1739 |

FOREIGN PATENT DOCUMENTS

| | | |
|---|---|---|
| JP | S58209343 A | 12/1983 |
| JP | H07184943 A | 7/1995 |
| JP | 3046822 B1 | 5/2000 |
| JP | 2009530053 A | 8/2009 |
| JP | 2013511353 A | 4/2013 |
| JP | 2014131735 A | 7/2014 |
| WO | 2011063257 A1 | 5/2011 |
| WO | 2014000661 A1 | 1/2014 |

OTHER PUBLICATIONS

First Office Action issued in connection with corresponding Japanese Patent Application No. 2018-511653, Mar. 12, 2019, 5 pages.

International Search Report and Written Opinion issued for PCT/US2016/049981, Dec. 8, 2016.

Second Office Action issued in connection with corresponding Japanese Patent Application No. 2018-511653, Sep. 10, 2019, 4 pages.

Office Action issued in connection with corresponding Canadian Patent Application No. 2,997,369, Sep. 19, 2019, 3 pages.

Second Examination Report issued in connection with corresponding Australian Patent Application No. 2018278965, Mar. 25, 2020, 3 pages.

Production Introduction—Innomed Shoulder Instruments—retractors & elevators, <URL:www.innomed.net/shoulder_rets_standard.htm#ShoulderSurgeryRetractorSystemShRets>, Published on Mar. 4, 2014 as per Wayback Machine.

Production Introduction—Innomed Small Bone Instruments—Foot & Ankle—retraction & exposure, <URL:www.innomed.net/smallbone_footankle_exposure.htm>, Published on Jan. 7, 2009 as per Wayback Machine.

Partial Search Report issued in connection with corresponding European Patent Application No. 16843015.5, Mar. 19, 2019, 11 pages.

* cited by examiner

CHEVRON OSTEOTOMY TOOLS AND METHODS

CROSS-REFERENCE TO RELATED APPLICATIONS

This application is a divisional of U.S. patent application Ser. No. 18/047,717, filed Oct. 19, 2022, which is a divisional of U.S. patent application Ser. No. 15/756,446, filed Feb. 28, 2018 (now U.S. Pat. No. 11,504,139), which is a national phase entry under 35 U.S.C. § 371 of international patent application no. PCT/US2016/049981, filed Sep. 1, 2016 which claims benefit under 35 U.S.C. § 119(e) to U.S. Provisional Application No. 62/213,161, filed Sep. 2, 2015, and entitled "CHEVRON OSTEOTOMY TOOLS AND METHODS," the entireties of which is are incorporated herein by reference.

BACKGROUND

Current procedures to perform a chevron osteotomy include the use of an osteotome/periosteal elevator. The use of the osteotome elevator is less than ideal, as the length, contours, tip, and sharpness, and overall ergonomics of the osteotome elevator are not configured for chevron osteotomy and may result in damage to soft tissue and/or bone. The osteotome elevator is typically round and prone to rotation during use, making the osteotome elevator difficult to operate with a single hand, as is common during chevron procedures.

Current procedures for a chevron osteotomy further fail to provide ideal fixation of one or more permanent fixation members. Displacement of bone portions during the osteotomy procedure, such as through the use of an elevator, can make fastener placement difficult.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1B:
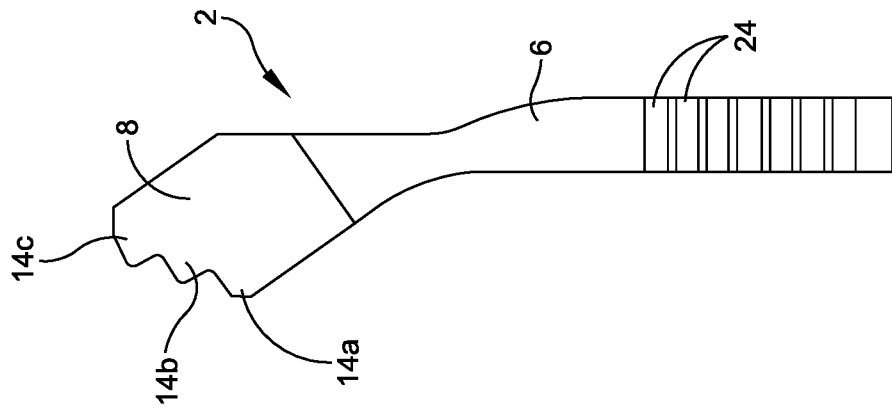
FIGS. 1A-1G illustrate one embodiment of a targeting guide for use in a surgical procedure, such as a chevron osteotomy, in accordance with the present disclosure
Figure 1A:
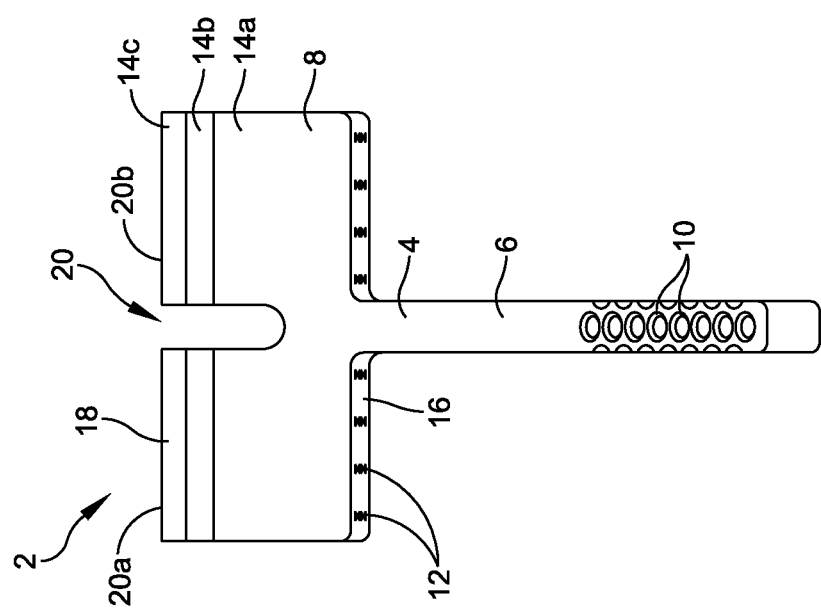
Figure 1C:
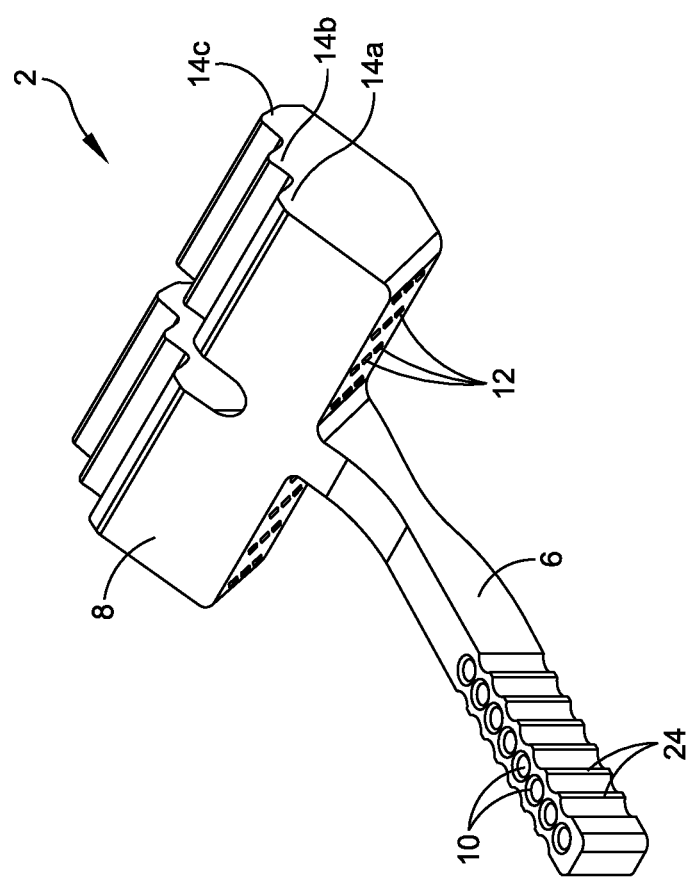

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

In various embodiments, a displacement tool for use in an osteotomy procedure is disclosed. The displacement tool includes a body having a handle portion and a displacement portion. The displacement portion extends longitudinally from a first end of the handle portion. The displacement portion has a predetermined curve. In some embodiments, the displacement portion has a rounded distal tip. In other embodiments, the displacement portion has a pointed distal tip. The displacement tool is sized and configured to displace a portion of a toe during an osteotomy without causing damage to soft tissue or bones of the toe.

In some embodiments, a surgical targeting guide for use in an osteotomy procedure is disclosed. The surgical targeting guide includes a body having handle and a head coupled to a distal end of the body. The handle extends substantially along a longitudinal axis. The handle defines a plurality of guide holes each sized and configured to receive a first elongate surgical instrument, such as a burr, therethrough. The head defines a plurality of targeting holes each sized and configured to receive a second elongate surgical instrument, such as a k-wire, therethrough. In some embodiments, the targeting holes extend through the head at a predetermined angle with respect to a longitudinal axis of the handle.

In some embodiments, a surgical screw guide for use in an osteotomy procedure is disclosed. The surgical screw guide includes a body including central section extending from a first end to a second end and defining a first slot between the first end and the second end and a first arm extending from the first end of the central section and defining a first hole. An alignment body is slidably received within the first slot defined by the central section of the body. A locking mechanism is coupled to a first end of the alignment body. The locking mechanism is configured to lock the alignment body at a location along a length of the first slot defined by the central section of the body.

FIGS. 1A-1G illustrate one embodiment of a surgical targeting guide 2 for use in a surgical procedure, such as, for example, a chevron osteotomy. The targeting guide 2 includes a body 4 having a handle 6 and a head 8. The handle 6 extends substantially along a longitudinal axis from a proximal end to a distal end. The handle 6 defines a plurality of positioning holes 10 each sized and configured to receive a first elongate surgical instrument, such as, for example, a burr, therethrough. The first elongate surgical instrument is coupled to an anatomical structure, such as a bone, and positions the surgical targeting guide 2 with respect to the anatomical structure.

In some embodiments, the plurality of positioning holes 10 are arranged substantially over a proximal half of the handle 6. The positioning holes 10 can extend through the handle 6 along an axis perpendicular to the longitudinal axis of the handle 6 and/or at an angle with respect to the longitudinal axis. For example, in some embodiments, the positioning holes 10 can extend through the handle 6 at any angle substantially between 0-90° with respect to the longitudinal axis of the handle 6.

In some embodiments, a head 8 is coupled to and/or formed integrally with a distal end of the handle 6. The head 8 can be coupled to the handle 6 at a predetermined angle, such as for example, any angle between 0-90°, such as 10°, 15°, 30°, 45°, 60°, 75°, 80°, 90°, and/or any other suitable angle. The head 8 defines a plurality of guide holes 12 extending therethrough. The plurality of guide holes 12 are each sized and configured to receive a second elongate surgical instrument, such as a k-wire, therethrough. The guide holes 12 extend from a first side to a second side of the head 8. For example, in some embodiments, one or more guide holes 12 extend from a proximal face/side of the head 8 to a distal side/face. In some embodiments, a first set of guide holes 10 can extend from a first face to a second face and a second set of guide holes 10 can extend from the first face to one or more additional faces of the head 8.

Figure 1E:
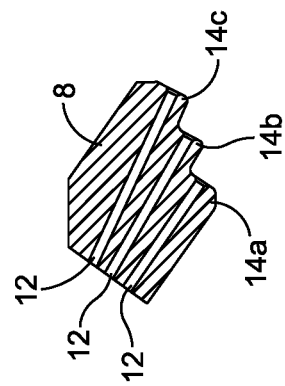
Figure 1D:
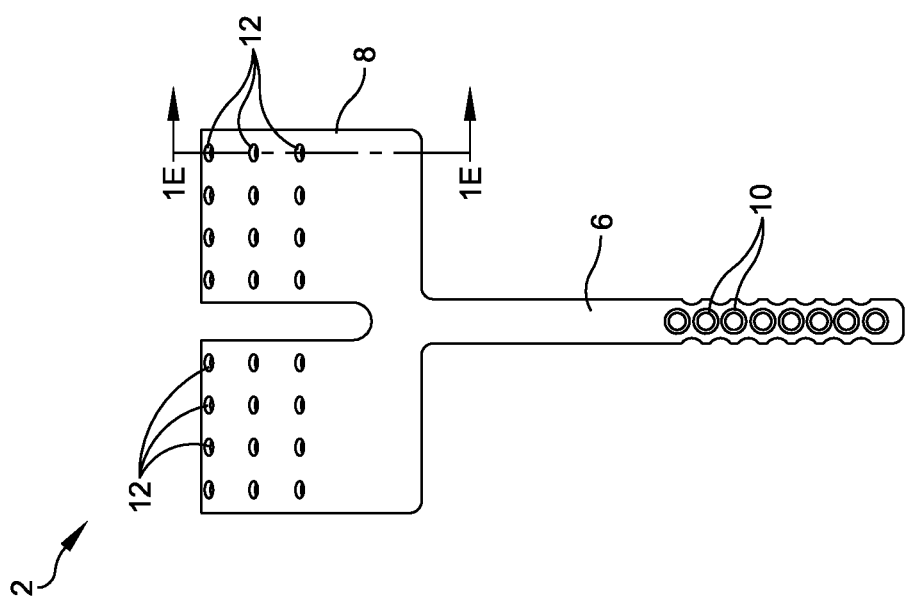
Figure 1G:
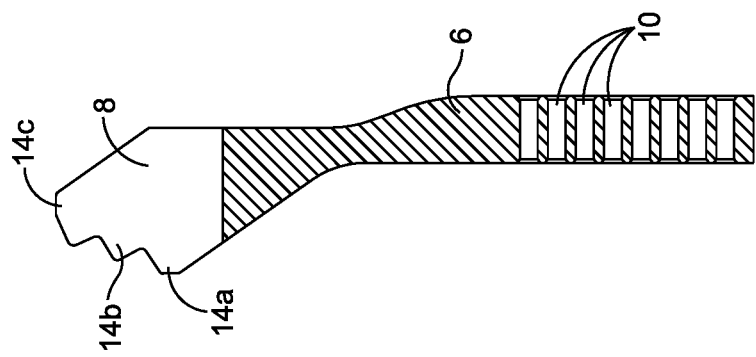
Figure 1F:
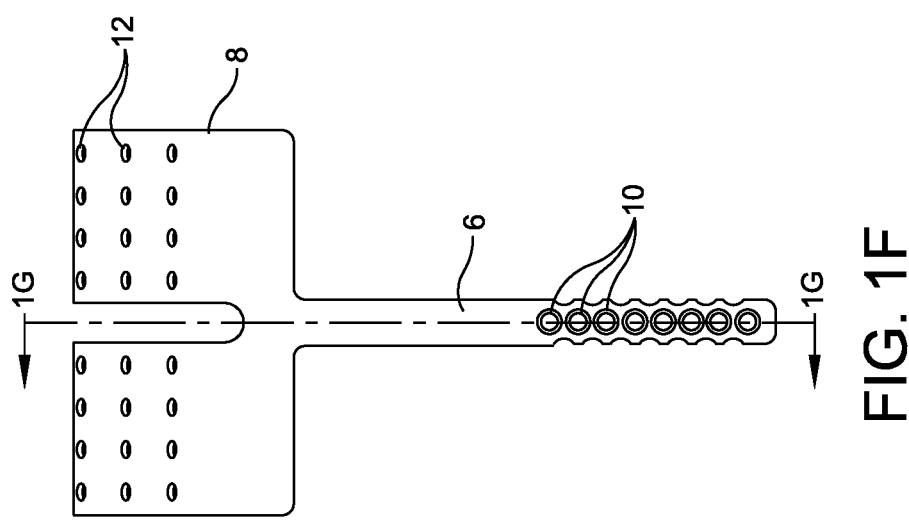

In some embodiments, the distal surface of the head 8 includes a stepped-configuration including a plurality of step levels 14a-14c. The plurality of step levels 14a-14c provide different positions and/or angles of insertion with respect to a k-wire 125 inserted through a guide hole 12. Each of the plurality of levels 14a-14c includes a plurality of guide holes 12 extending from proximal side 16 of the head 8 to a distal side 18. In some embodiments, the plurality of guide holes 12 through of the plurality of levels 14a-14c extend through the head 8 at a different angle, as illustrated in FIG. 1E. The plurality of guide holes 12 and step-levels 14a-14c allow a surgeon to select the best location for insertion of k-wires or other elongate surgical instruments during surgery.

In some embodiments, the head 8 includes a cutout 20 sized and configured to interface with a portion of an anatomical structure, such as, for example, one or more bones of the foot. The cutout 20 and the edges of the head 8 define one or more tines 20a, 20b. The cutout 20 is sized and configured to allow the tines 20a, 20b to be positioned on opposite sides of the anatomical structure. For example, in some embodiments, the cutout 20 is sized and configured to receive a metatarsal and/or one or more additional toe bones therein to position the tines 20a, 20b on opposite sides of the metatarsal.

In some embodiments, the body 4 of the targeting guide 2 is configured to guide one or more k-wires during a surgical chevron osteotomy. The targeting guide 2 is placed exterior of a foot at a surgical site. In some embodiments, at least one of the positioning holes 10 is placed over a first elongate surgical instrument, such as a burr, coupled to the anatomical structure to position the targeting guide 2. The first elongate surgical instrument can be coupled to the anatomical structure prior to and/or simultaneous with positioning of the targeting guide 2. After the targeting guide 2 is positioned at a surgical site, one or more k-wires are inserted through the k-wire holes 12 formed in the head 8 and anchored to one or more bones. The targeting guide 2 can be removed from the surgical site by sliding the targeting guide 2 over the k-wires and burr. In some embodiments, the handle 6 includes a plurality of gripping features 24 sized and configured to allow a user to securely grip the targeting guide 2 during a surgical procedure.

Figure 2:
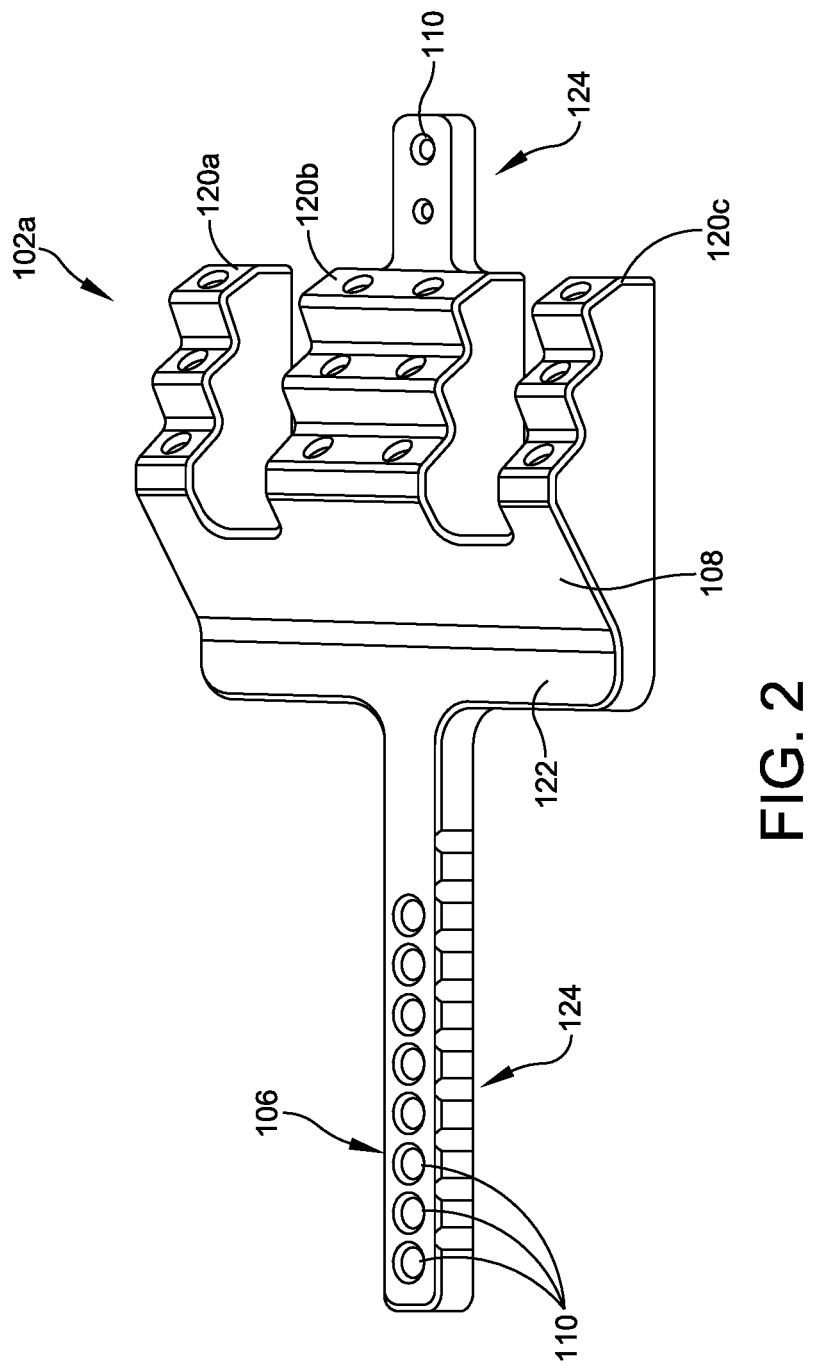
FIG. 2 illustrates one embodiment of a targeting guide including a head having three tongs, in accordance with the present disclosure.
Figure 3:
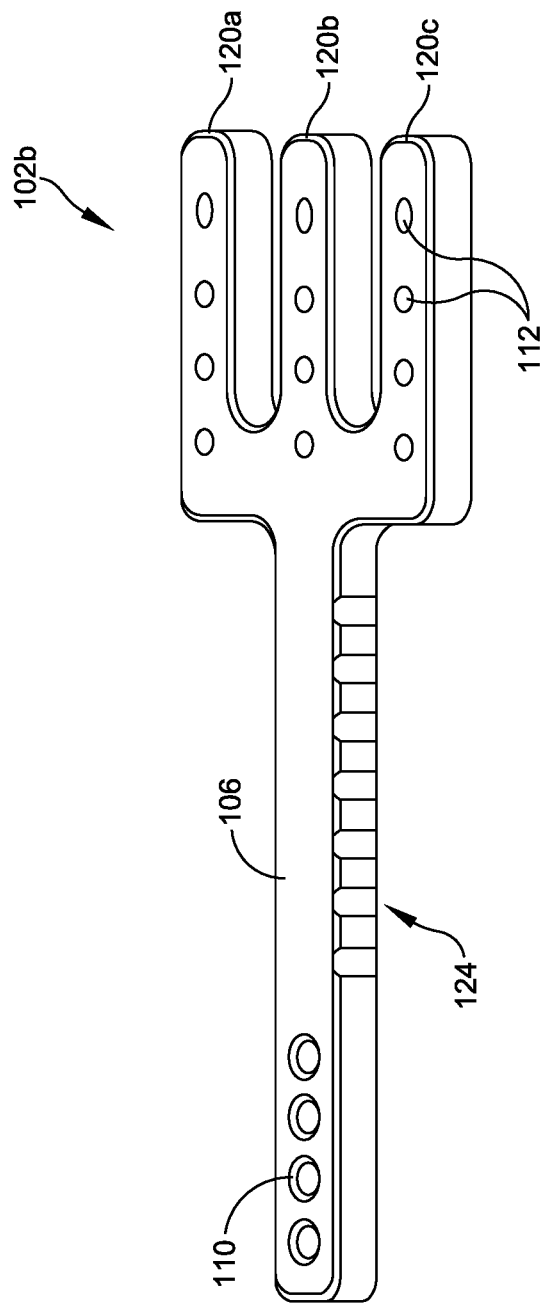
FIG. 3 illustrates one embodiment of a targeting guide having a flat head, in accordance with the present disclosure.
Figure 4:
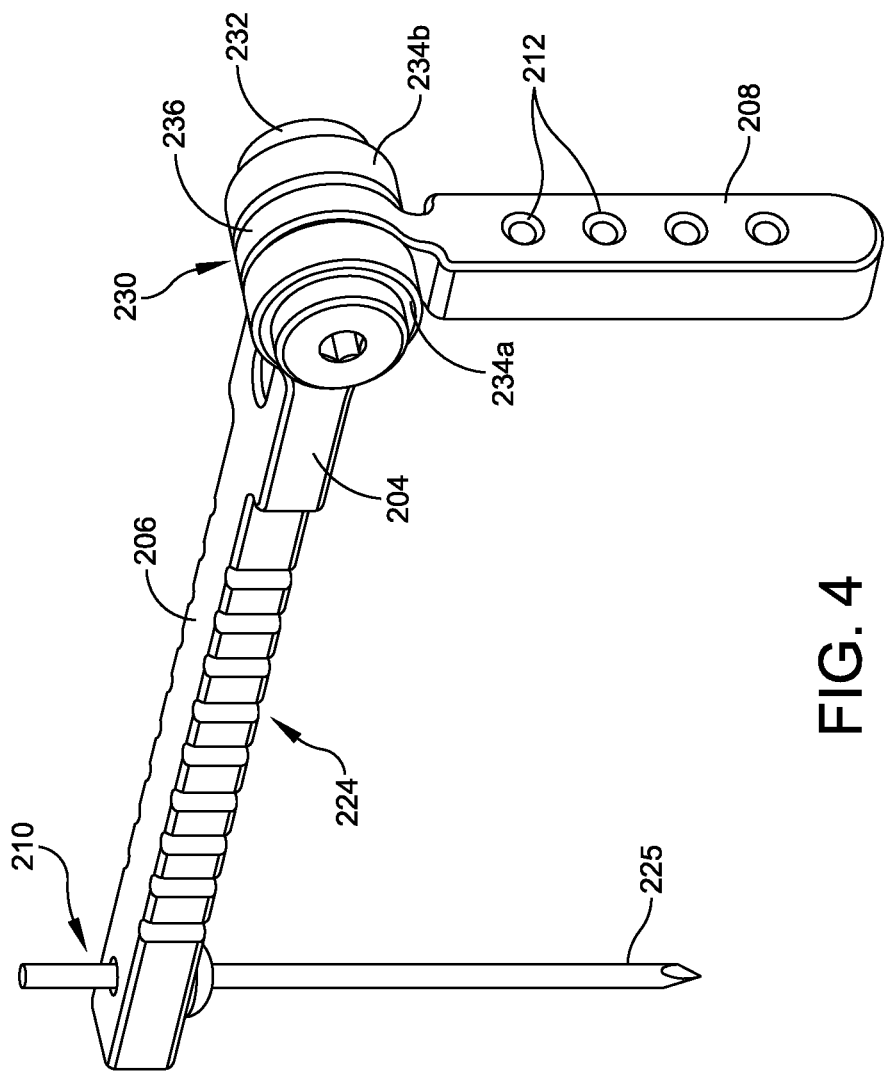
FIG. 4 illustrates one embodiment of a targeting guide having a rotatable head portion, in accordance with the present disclosure.

FIGS. 2-4 illustrate alternative embodiments of the targeting guide 2, in accordance with the present disclosure. FIGS. 2 and 3 illustrate embodiments of a targeting guide 102 including a head 108 having three tongs 120a-120c. The targeting guide 102a illustrated in FIG. 2 is similar to the targeting guide 2. The head 108 of the targeting guide 102a has three tines 120a-120c extending from a common base 122. In some embodiments, an additional anchoring section 124 extends from a central tine 120b of the head 108. A plurality of k-wire holes 112 extend from a first side of the head 108 (shown) to a second side of the head 108 (not shown).

The targeting guide 102b illustrated in FIG. 3 includes a flat head having a plurality of k-wire holes therethrough. In some embodiments, the plurality of guide holes 112 extend through the flat head 108 at a predetermined angle. For example, in various embodiments, the plurality of guide holes 112 can extend through the flat head 108 at any angle substantially between 0-90°, such as 15°, 30°, 45°, 60°, 75°, 90°, and/or any other suitable angle. In the illustrated embodiment, each of the sections 120a-120c includes four guide holes 112, although it will be appreciated that each of the sections 120a-120c of the head 108 can include any suitable number of guide holes 112.

FIG. 4 illustrates one embodiment of a targeting guide 202 having a rotatable head 208, in accordance with the present disclosure. The targeting guide 202 includes a body 204 having a handle 206 rotatably coupled to a head (or targeting portion) 208. The body 204 includes at least one positioning hole 210 sized and configured to receive a first elongate surgical instrument, such as a guide pin 225 or a burr, therein. In some embodiments, the body 204 includes a plurality of gripping features 224. The body 204 is rotatably coupled to the head 208 by a rotatable joint 230. The rotatable joint 230 may comprise a pin 232 inserted one or more pin slots 234a, 234b, 236 formed in the handle 206 and/or the head 208. The head 208 rotates about the rotatable joint 230 to position the targeting guide 208 with respect to a portion of patient's anatomy. The head 208 includes a plurality of guide holes 212 each sized and configured to receive a second elongate surgical instrument, such as a k-wire, therethrough.

Figure 5C:
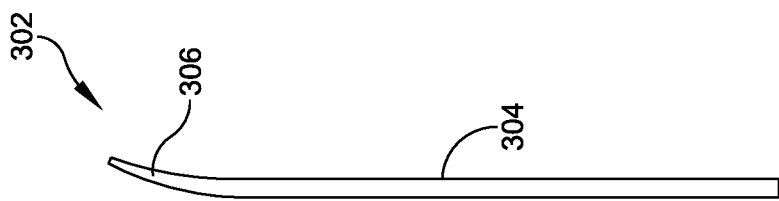
FIGS. 5A-5C illustrate one embodiment of an displacement elevator, in accordance with the present disclosure.
Figure 5B:
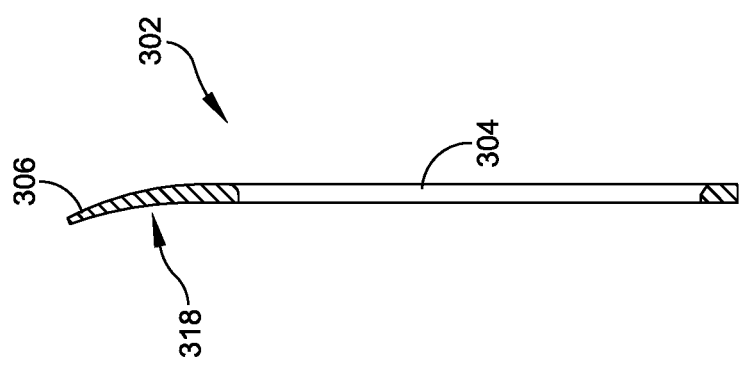
Figure 5A:
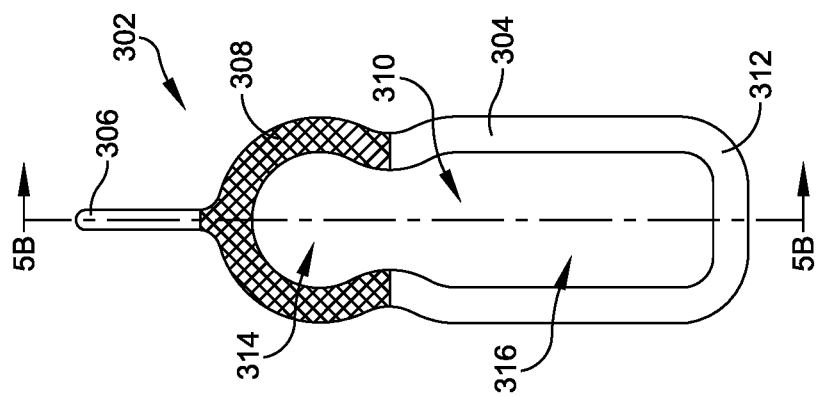

FIGS. 5A-5C illustrate an embodiment of a surgical elevator 302, in accordance with the present disclosure. The elevator 302 includes a body 304 having a displacement tip 306 extending therefrom. The displacement tip 306 defines a predetermined radius of curvature 318. In some embodiments, the body 304 includes a distal portion 308 and a proximal portion 312 configured to allow flexing of the elevator 302 between the distal portion 308 and the proximal portion 312. The body 304 defines an inner cavity 310. In some embodiments, the inner cavity 310 is sized and configured to receive one or more anatomical features of a patient therein, such as, for example, one or more bones. The inner cavity 310 allows the elevator 302 to be positioned and/or flexed beyond the plane of a patient's foot.

In some embodiments, the elevator 302 is configured to generate and/or facilitate generation of an osteotomy in a bone, such as a metatarsal. The displacement tip 306 is sized and configured to be inserted into a cut formed in a bone. The body 304 is rotated in a first direction to force a first bone portion away from a second bone portion to form an osteotomy. In some embodiments, the inner cavity 310 defines a first cavity portion 314 and a second cavity portion 316 designed to receive one or more anatomical structures, such as a bone portion, when the body 304 is rotated. In some embodiments, the first and/or second cavity portions 314, 316 are sized and configured to receive a portion of a metatarsal therein.

Figure 6:
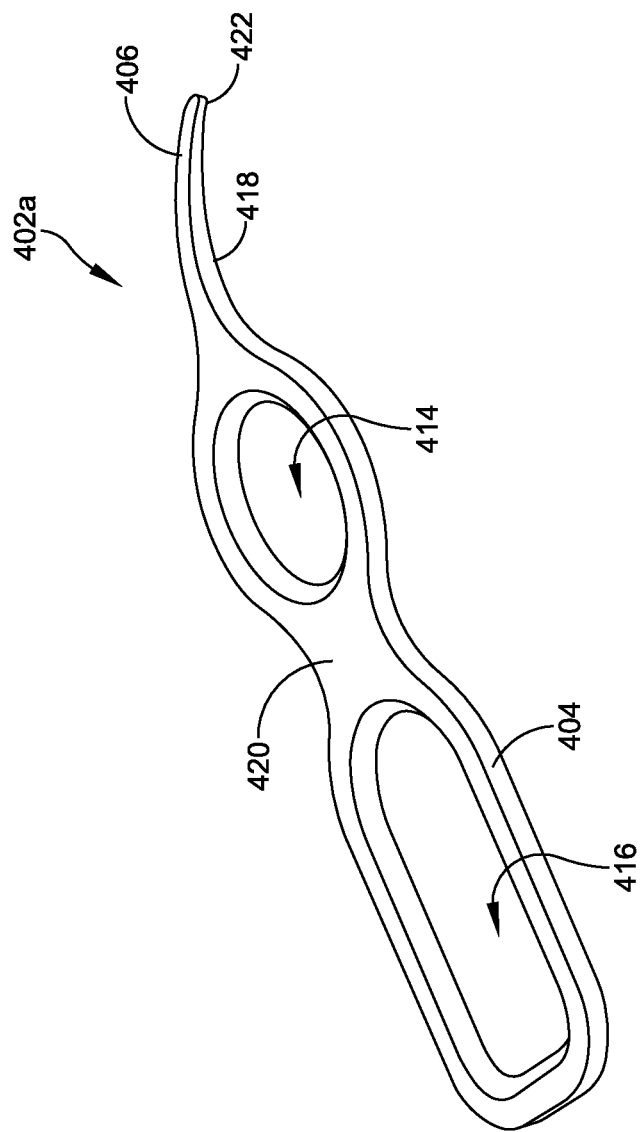
FIG. 6 illustrates one embodiment of an displacement elevator having a solid neck portion, in accordance with the present disclosure.
Figure 7:
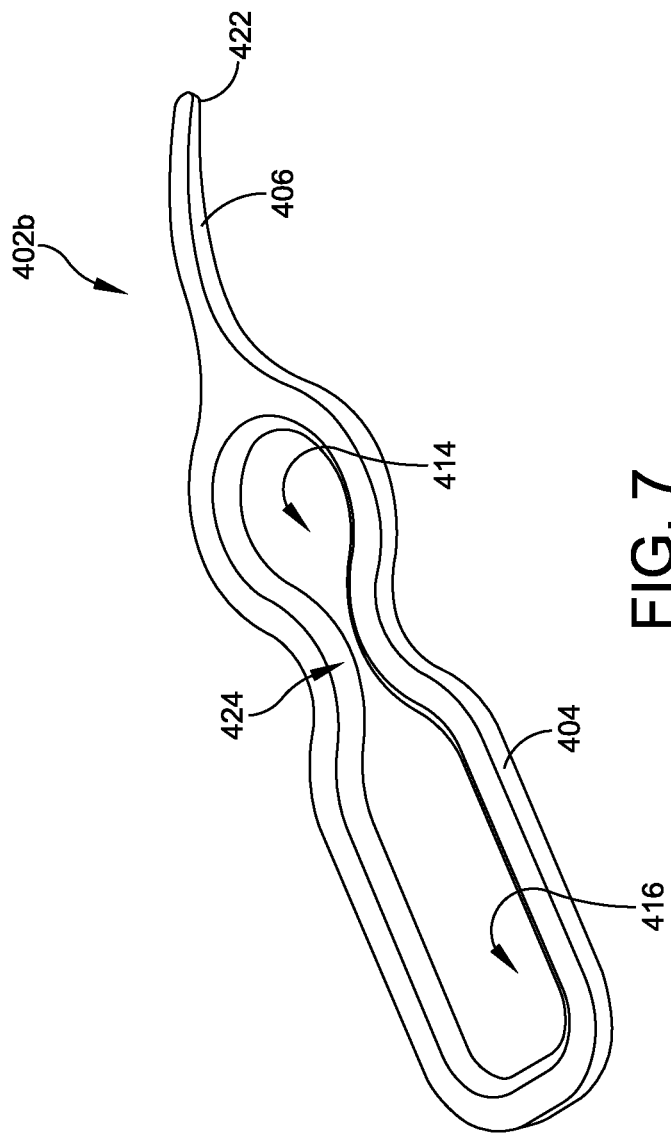
FIG. 7 illustrates one embodiment of a displacement elevator having an open end and an open neck between a first cavity and a second cavity, in accordance with the present disclosure.

FIGS. 6-11 illustrate various alternative embodiments of a surgical elevator 402. The surgical elevator 402 is similar to the surgical elevator 302 discussed above, and similar description is not repeated herein. FIG. 6 illustrates one embodiment of an elevator 402a having a first inner cavity 414 and a second inner cavity 416 separated by a closed neck 420 of the body 404. The elevator 402 includes a body 404 and a displacement tip 406 extending therefrom. A distal end 422 of the displacement tip 406 is sized and configured to be received within a cut formed in a bone, such as, for example, a metatarsus. FIG. 7 illustrates one embodiment of an elevator 402b similar to the elevator 302, and similar description is not repeated herein. The elevator 402b has a smaller neck opening 418 as compared to the elevator 302 of FIGS. 5A-5C. The smaller neck opening 424 provides a different flex profile to the body 404 of the elevator 402b. In some embodiments, the smaller neck opening 424 increases flex at the neck 420.

Figure 8:
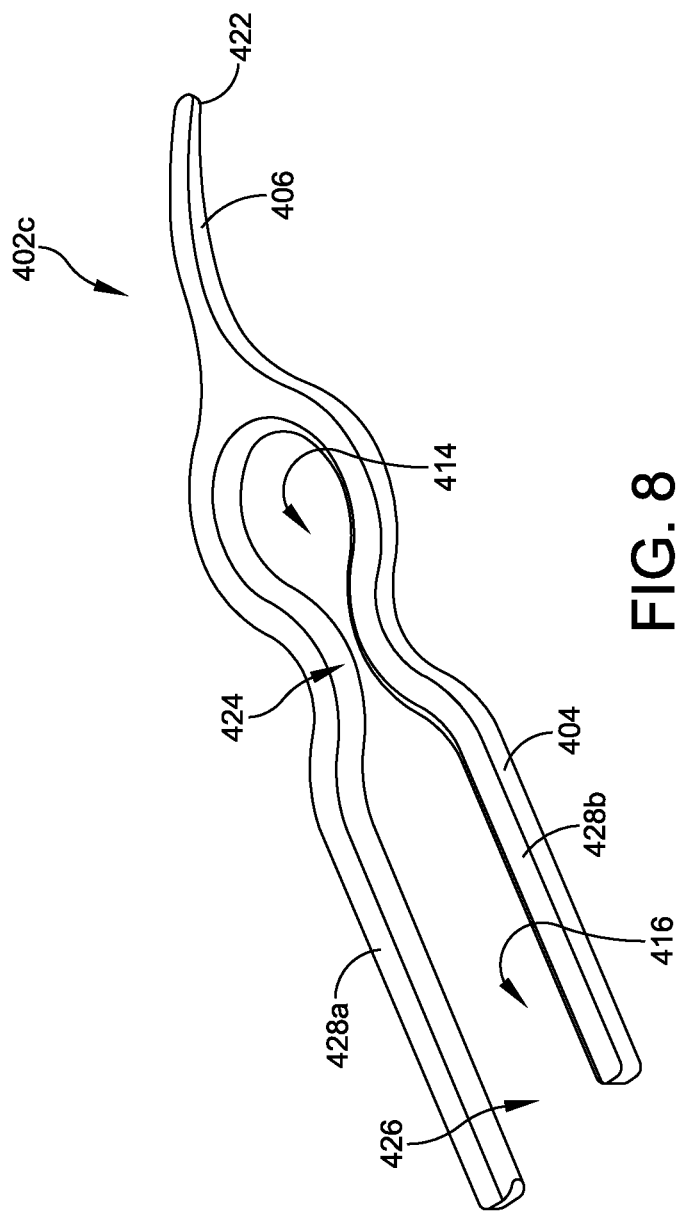
FIG. 8 illustrates one embodiment of a displacement elevator having an open end, in accordance with the present disclosure.
Figure 9:
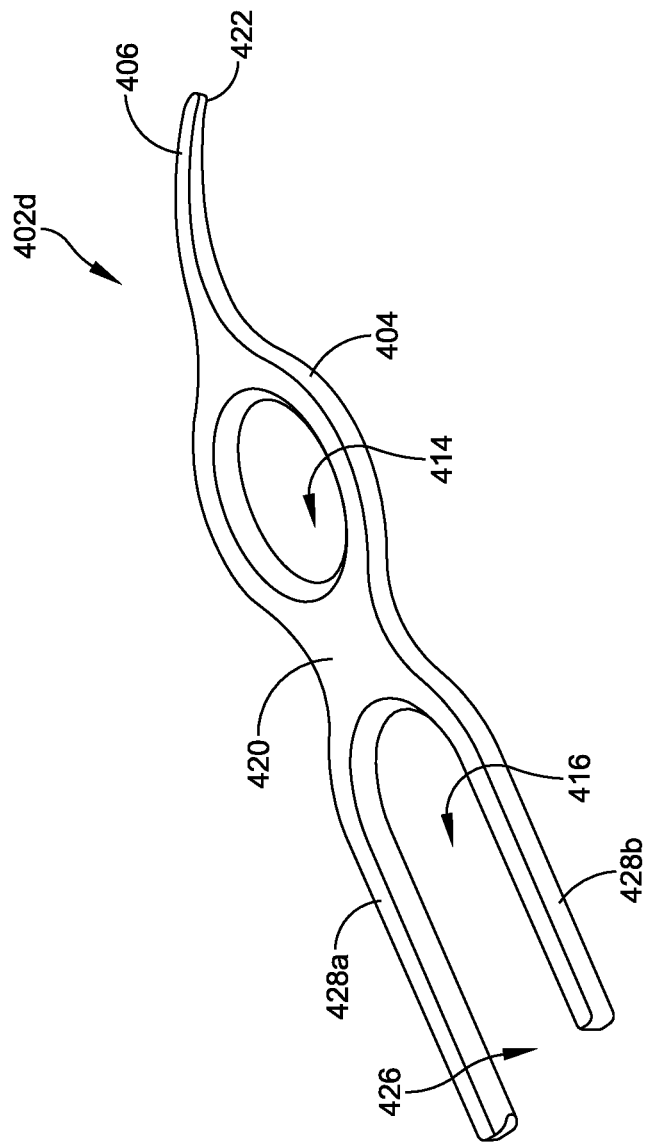
FIG. 9 illustrates one embodiment of a displacement elevator having an open end and a solid neck, in accordance with the present disclosure.

FIG. 8 illustrates one embodiment of an elevator 402c having an open proximal end 426. The open proximal end 426 allows a first side 428a of the body 404 to flex independent of and/or out of plane of a second side 428b of the body 404. FIG. 9 illustrates one embodiment of an elevator 402d having an open proximal end 426 and a closed neck 420. The different open/closed necks and/or open/closed ends of the various elevators 402 illustrated in FIGS. 6-9 provide different flex and force profiles. In some embodiments, the open proximal end 426 allows the elevator 402c, 402d to flex at a greater angle with respect to the metatarsal.

Figure 10:
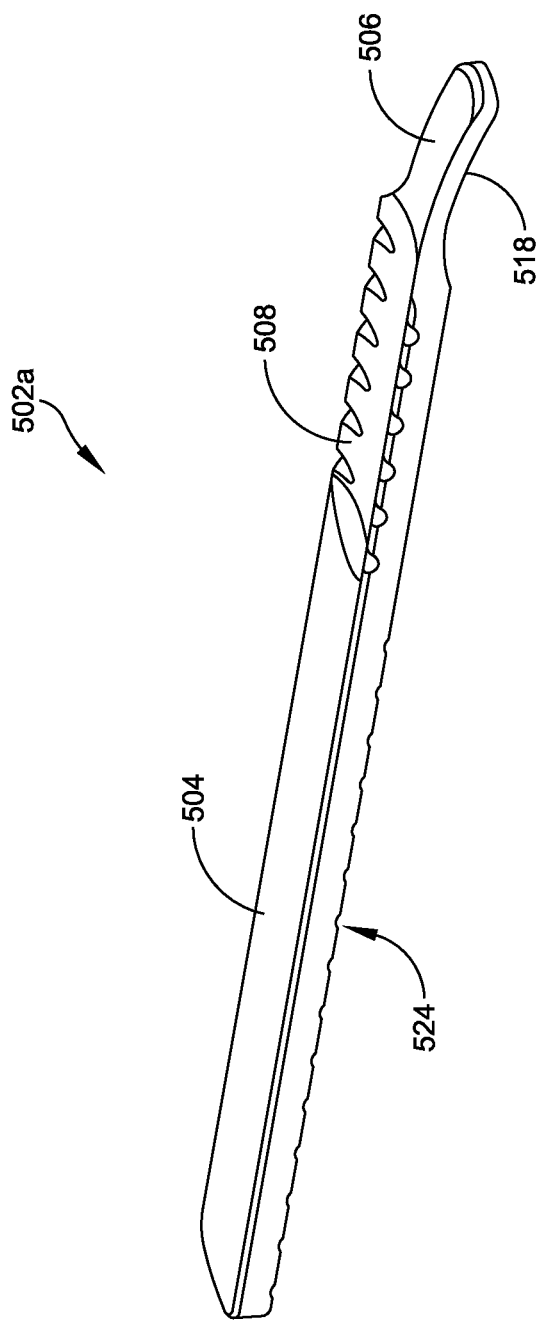
FIG. 10 illustrates one embodiment of a displacement elevator including a securing section for securing a portion of a toe, in accordance with the present disclosure.
Figure 11:
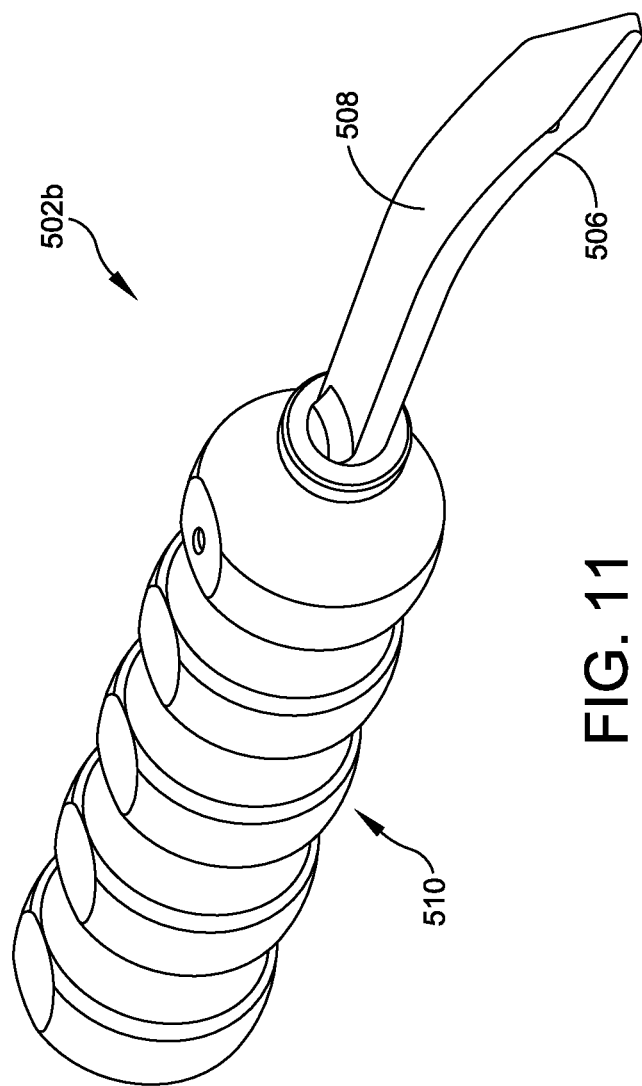
FIG. 11 illustrates one embodiment of a displacement elevator including a securing section and a gripping handle, in accordance with the present disclosure.

FIG. 10 illustrates one embodiment of a longitudinal elevator 502. The longitudinal elevator 502 includes a longitudinal body 504 extending substantially along a longitudinal axis. A displacement tip 506 extends from a distal end of the longitudinal body 504. The displacement tip 506 is sized and configured for insertion into a cut formed in a bone, such as, for example, a metatarsal. The longitudinal body 504 can be rotated by a user to displace a first portion of a bone from a second portion of a bone to form an osteotomy. In some embodiments, the longitudinal body 504 defines a bone retaining section 508. The bone retaining section 508 can comprise a concave and/or open area for securing a portion of a bone, such as a distal portion of a metatarsal, after displacement of the bone portion to form an osteotomy. For example, in the illustrated embodiment, the longitudinal body 504 defines a concave retaining section 508 sized and configured to secure a distal portion of a metatarsal bone after the displacement tip 506 displaces a first portion of the metatarsal from a second portion of the metatarsal to form an osteotomy. In some embodiments, as shown in FIG. 11, the longitudinal handle 504 is surrounded by a large, gripping handle 510 to provide additional gripping surface to a user.

Figure 12A:
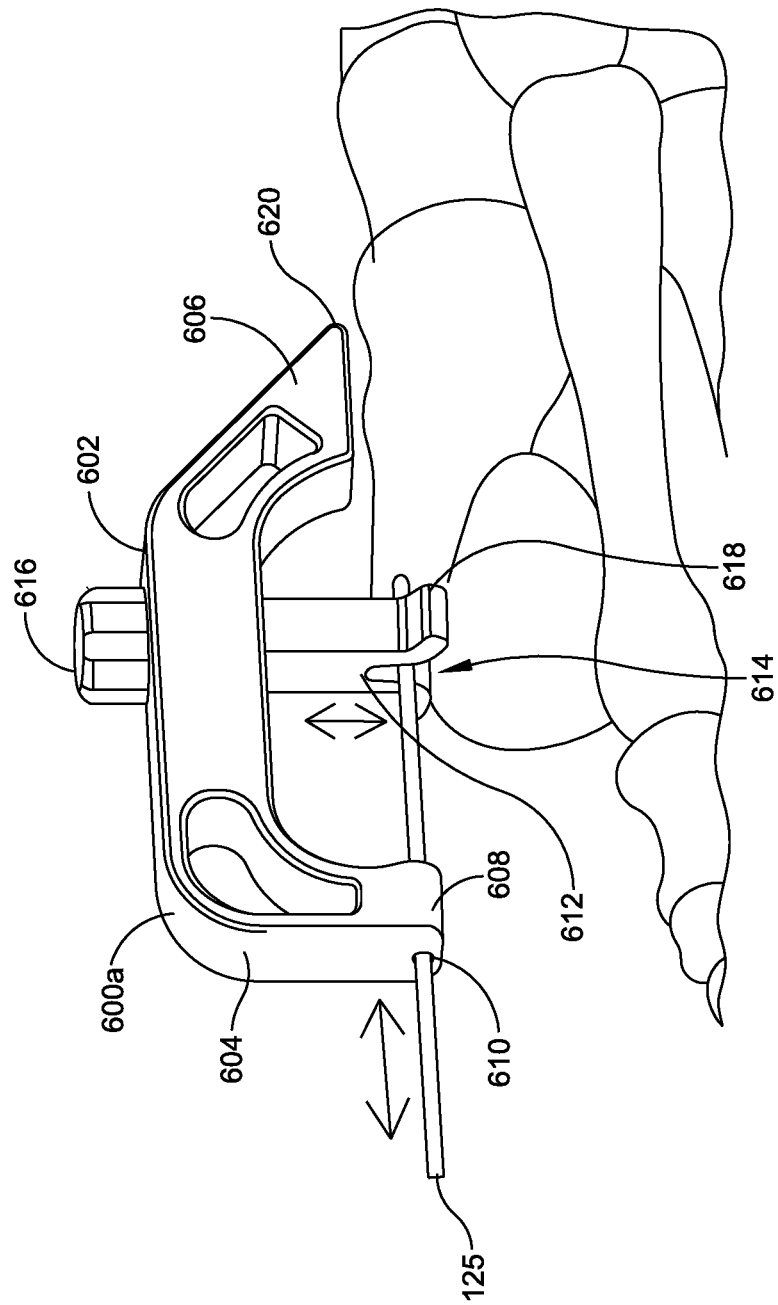
FIG. 12A illustrates one embodiment of a surgical screw placement guide, in accordance with the present disclosure.
Figure 12B:
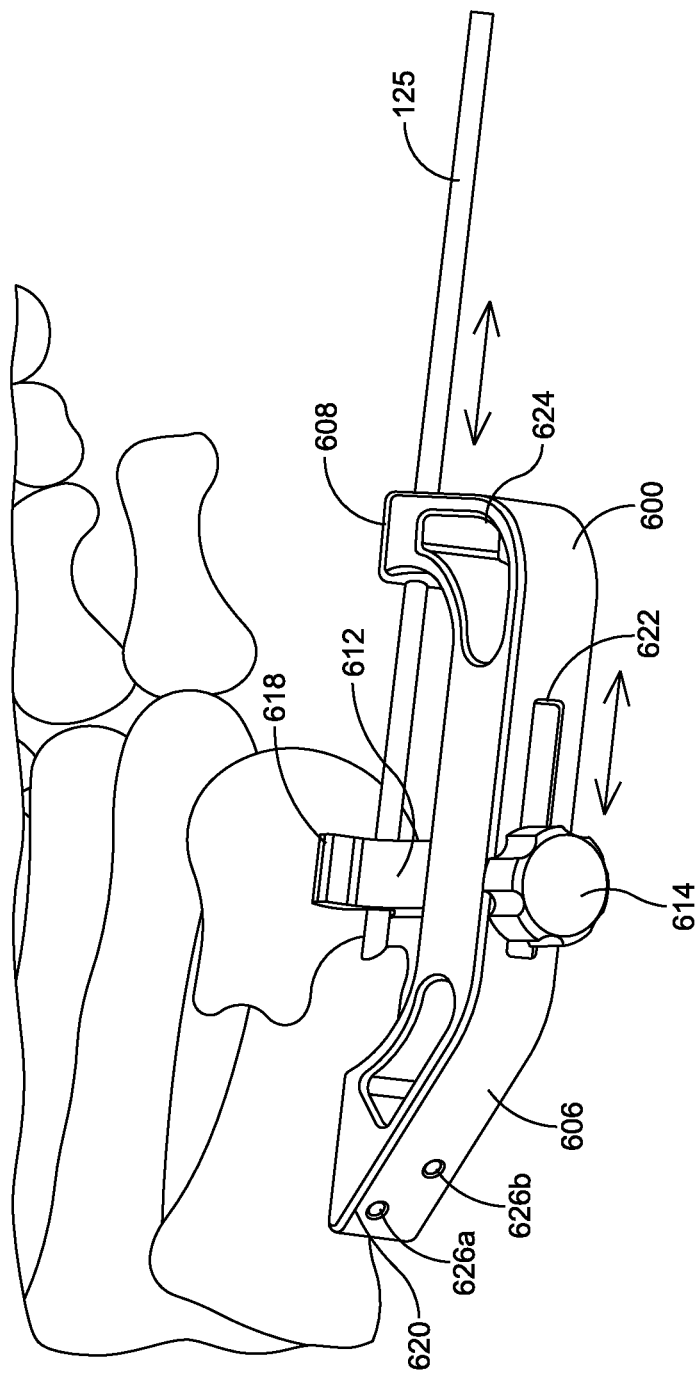
FIG. 12B is a top view of the surgical screw placement guide of FIG. 12A, in accordance with the present disclosure.
Figure 12C:
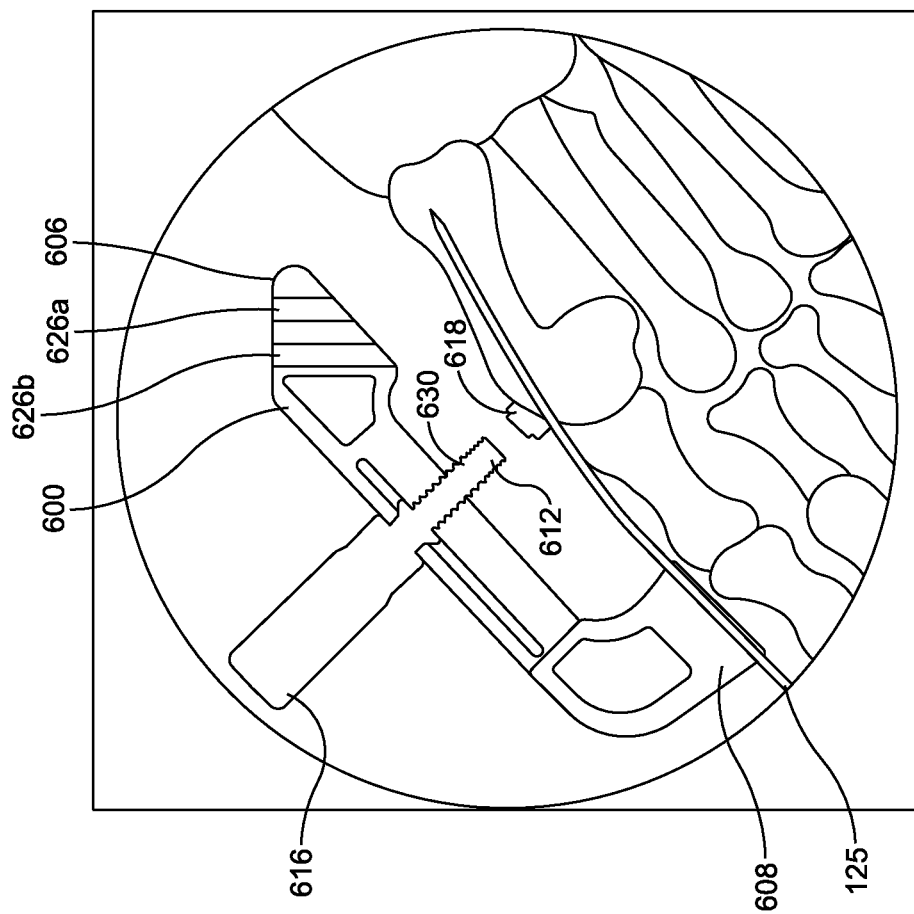
FIG. 12C is a radiographic view of the surgical screw placement guide of FIG. 12A adjacent to a bone, in accordance with the present disclosure.

FIGS. 12A-12C illustrates one embodiment of a surgical screw guide 600a configured to provide positioning of one or more fasteners, in accordance with the present disclosure. The surgical guide 600a includes a body 602. The body 602 defines a central section 603 extending from a first end 604 to a second end 606. The central section 603 defines a first slot 622 between the first end 604 and the second end 606. The body 602 includes a first arm 608 extending from the first end 604 of the central section 603 and defining a first hole 610. The first hole 610 is sized and configured to receive a guide wire 125 therethrough. In some embodiments, the first arm 608 extends perpendicularly from the central section, although it will be appreciated that the first arm can extend at any suitable angle, such as any angle between 0-90°.

In some embodiments, an alignment body 612 is slidably received within the first slot 622 defined by the central section 603 of the body 602. The alignment body 612 is configured to move along the length of the first slot 622 and can be configured to move transversely relative to a longitudinal axis defined by the first slot 622. A locking mechanism 616 is coupled to a first end of the alignment body 612. The locking mechanism 616 is configured to lock the alignment body 612 at a variable location along a length of the first slot 622. The locking mechanism 616 can include any suitable locking mechanism, such as, for example, a thumb screw, a wing nut, and/or any other suitable locking mechanism.

In some embodiments, the alignment body 612 defines a second slot 614 that inwardly extends from a second end of the alignment body 612. The first hole 610 and the second slot 614 are configured to receive an elongate surgical instrument, such as guide wire 125, therein. In some embodiments, the first hole 610 and the second slot 614 are aligned along a longitudinal axis. In some embodiments, the elongate surgical instrument has a radius of curvature and/or can selectively be bent. The first hole 610 and the second slot 614 can be positioned to receive an elongate surgical instrument having a predetermined radius of curvature.

In some embodiments, the body 602 includes a second arm 620 extending from the second end 606 of the central section 603. In some embodiments, the second arm 620 defines one or more holes 626a, 626b extending from a first side of the body 602 to a second side. The first and second holes 626a, 626b each extend through the second arm 620 along a longitudinal axis. In some embodiments, the longitudinal axes of the first and second holes 626 are parallel. In some embodiments, the longitudinal axes of the first and second holes 626a, 626b extend at a predetermined angle, such as, any angle between 0-90°.

Figure 13A:
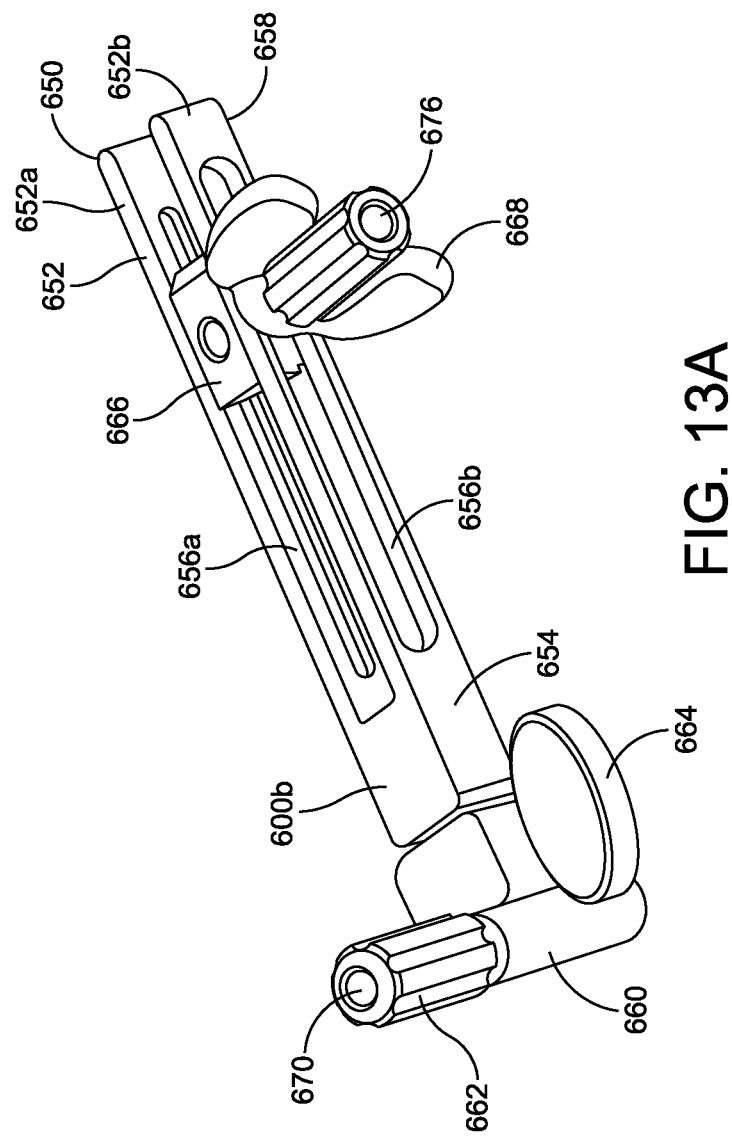
FIG. 13A illustrates one embodiment of a surgical screw placement guide, in accordance with the present disclosure.
Figure 13B:
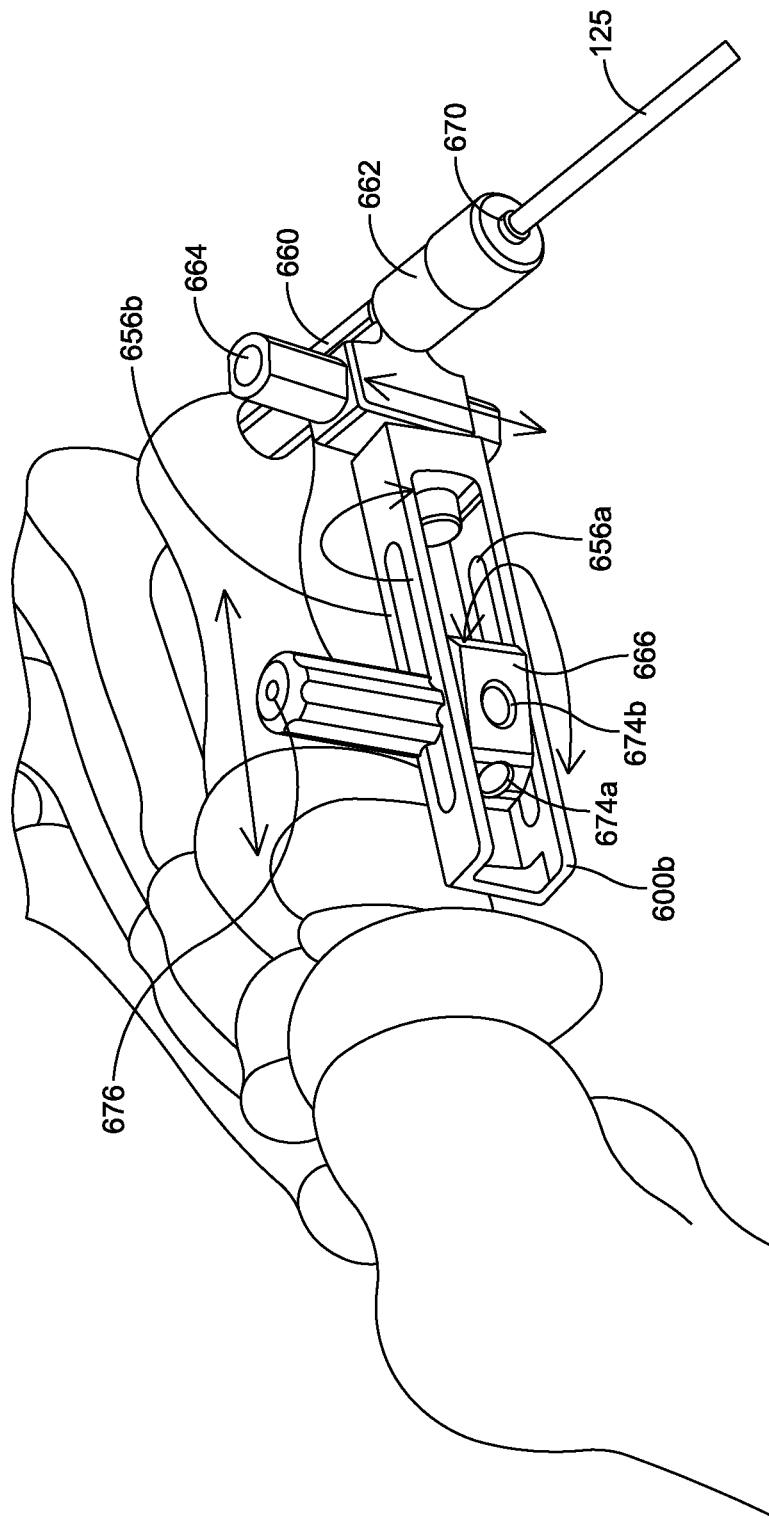
FIG. 13B illustrates the surgical screw placement guide of FIG. 13A in contact with one or more bones, in accordance with the present disclosure.
Figure 13C:
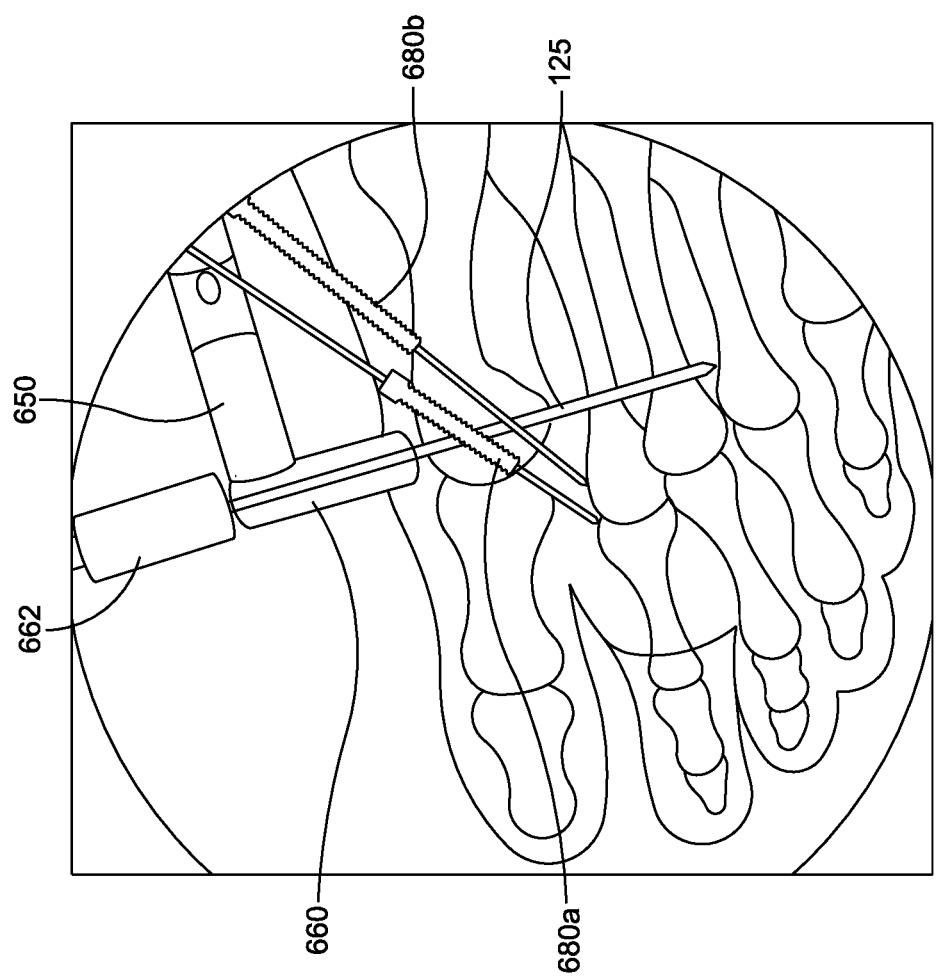
FIG. 13C illustrates a radiographic view of the surgical screw placement guide of FIG. 13A adjacent to one or more bones, in accordance with the present disclosure.

FIGS. 13A-13C illustrate another embodiment of a surgical guide 600b, in accordance with the present disclosure. The surgical guide 600b includes a body 650. The body 650 defines a central section 652 extending from a first end 654 to a second end 658. The central section 652 defines a first slot 656a between the first end 654 and the second end 658. The body 650 includes a first arm 660 extending from the first end 654 of the central section 652 and defining a first hole 670. The first hole 670 is sized and configured to receive a second elongate surgical instrument, such as a k-wire, therethrough. In some embodiments, the first hole 670 extends through the first arm 660 in a plane that is perpendicular to a longitudinal direction of the central section 652.

In some embodiments, an alignment body 666 is slidably received within the first slot 656a defined by the central section 652 of the body 650. The alignment body 666 is configured to slidably move within the first slot 656a and can be further configured to move transversely relative to a longitudinal axis defined by the first slot 656a. A locking mechanism 668 is coupled to a first end of the alignment body 666. The locking mechanism 668 is configured to lock the alignment body 666 at a variable location within the first slot 656a. The locking mechanism 668 can include any suitable locking mechanism, such as, for example, a thumb screw, a wing nut, and/or any other suitable locking mechanism.

In some embodiments, the body 650 defines a second slot 656b. The first slot 656a can extend through a first side and a second side of a first portion 652a of the central section 652 and the second slot 656b can extend through a third side and a fourth side of a second portion 652b of the central section 652 of the body. In some embodiments, the first slot 656a and the second slot 656b are parallel, although it will be appreciated that, in some embodiments, the first slot 656a and the second slot 656b can be offset. Each of the first slot 656a and the second slot 656b have a predetermined longitudinal length. In some embodiments, the longitudinal length of the first slot 656a and the second slot 656b is equal.

In some embodiments, the alignment body 666 includes a rotatable portion 672 configured to rotate or pivot about an axis that is oriented perpendicularly with respect to a longitudinal direction of the central section 652. The rotatable portion 672 can be positioned between the first slot 656a and the second slot 656b. The alignment body 666 can define one or more holes extending therethrough. For example, in some embodiments, the rotatable portion 672 includes a first hole 674a that extends through the rotatable portion 672 in a first direction and a second hole 674b that extends through the rotatable portion 672 in a second direction. In various embodiments, the first direction can be perpendicular to the second direction and/or positioned at an angle substantially between 0-90° with respect to the second direction. In some embodiments, the first hole 674a and the second hole 674b are sized and configured to receive fasteners 680a, 680b therethrough. The first and second holes 674a, 674b guide the fasteners 680a, 680b into appropriate positions for fixing an osteotomy. In some embodiments, the alignment body 666 defines a third hole 676 extending through the alignment body 666 along a longitudinal axis that is perpendicular to a plane defined by the first hole 674a and/or the second hole 674b.

In some embodiments, the first arm 660 is configured to rotate about a longitudinal axis defined by the central section 652 of the body 650. The position of a longitudinal axis of the first hole 670 extending through the first arm 660 can be adjusted by rotating the first arm 660 about the longitudinal axis of the central section 652. In some embodiments, the first arm 660 is configured to slide in one or more directions that are perpendicular to the longitudinal axis defined by the central section 652. For example, in some embodiments, a center point of the first arm 660 can be adjusted laterally with respect to the longitudinal axis defined by the central section 652.

Figure 14:
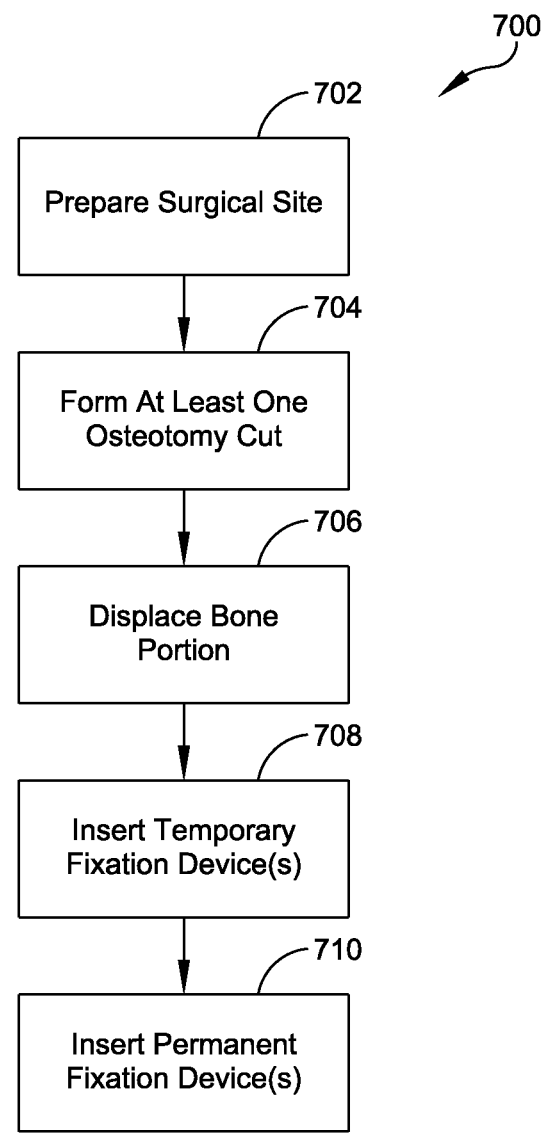
FIG. 14 illustrates one embodiment of a method of performing a chevron osteotomy, in accordance with the present disclosure.

In some embodiments, one or more of the surgical targeting guides, surgical elevators, and/or surgical screw guides disclosed herein can be used to perform a surgical procedure, such as, for example, a chevron osteotomy. FIGS. 14-15G illustrate one embodiment of a chevron osteotomy method 700, in accordance with some embodiments. At step 702, a cut is formed in a metatarsal at a surgical site 800. As shown in FIG. 15A, a foot 802 comprises a plurality of bones, including a first toe 804 having a plurality of phalanges 806a-806b, a metatarsus 808, and a plurality of cuneiforms 810. A portion of the metatarsal 808 is removed during the initial cut. In some embodiments, one or more continuous and/or non-continuous cuts are made to form a chevron-shaped osteotomy. For example, in some embodiments, rotation of the burr 812 about a point of entry into the patient's anatomy is used to form a dorsal limb and a plantar limb of a chevron osteotomy. The plane of the osteotomy is defined by the entry cut of the burr 812 into the metatarsal 808. The burr 812 may be left in a final position to act as a guide for one or more additional surgical elements.

Figure 15B:
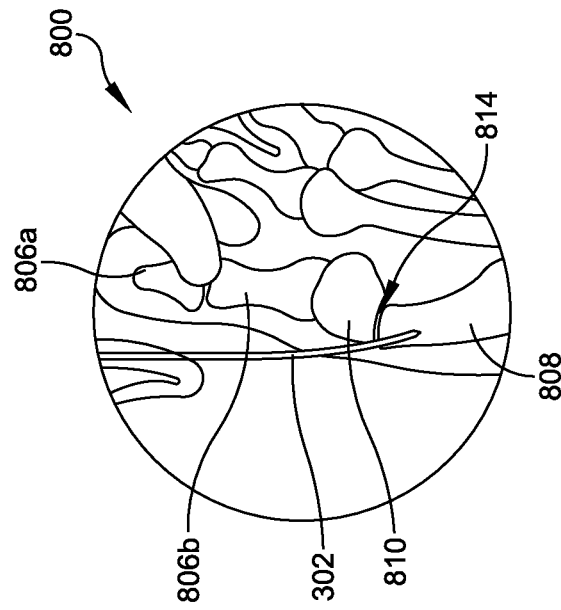
FIGS. 15A-15G illustrates various steps of the method of FIG. 14, in accordance with the present disclosure.
Figure 15A:
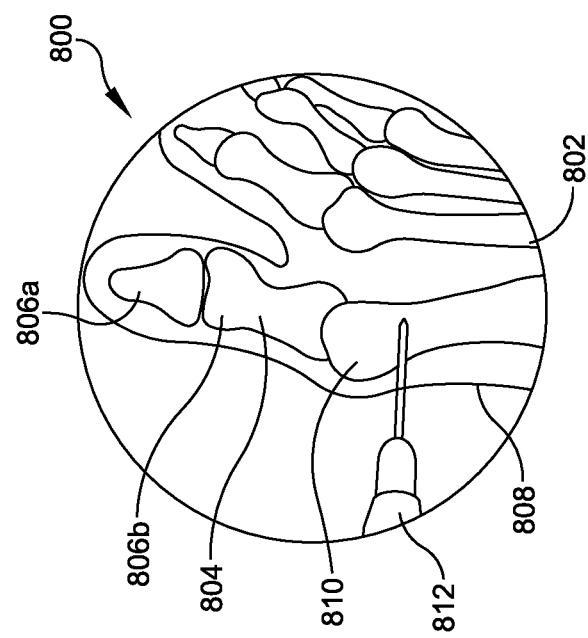
Figure 15E:
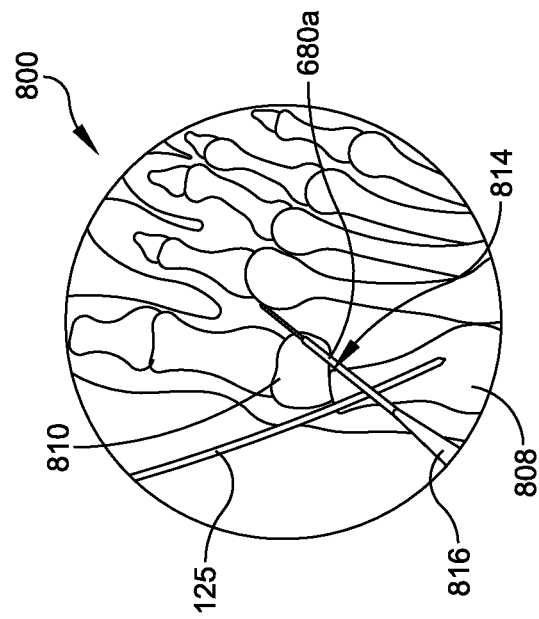
Figure 15C:
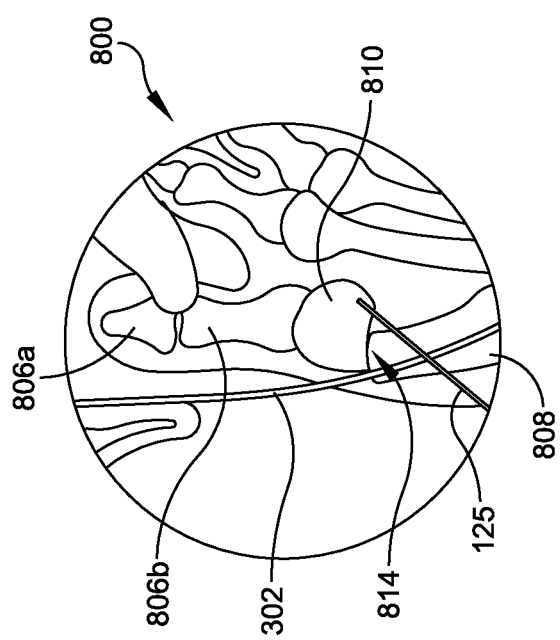
Figure 16A:
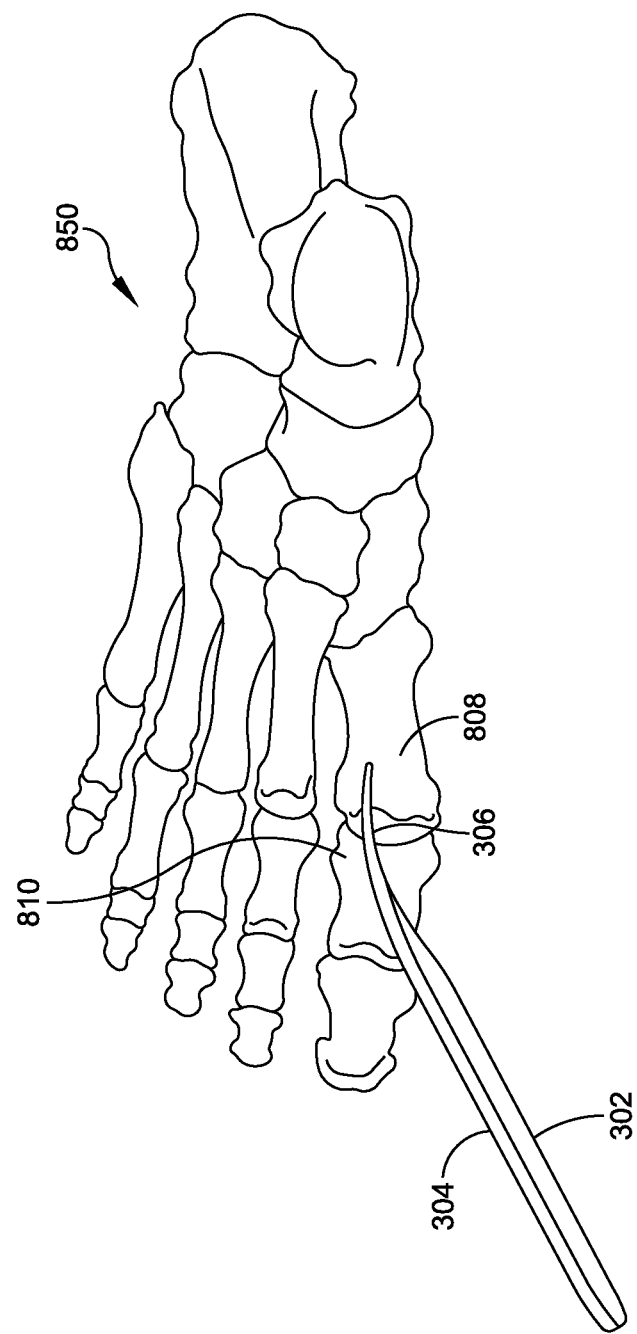
FIGS. 16A-16B illustrate one embodiment of a step of displacing a metatarsal during the method of FIG. 14, in accordance with the present disclosure.
Figure 16B:
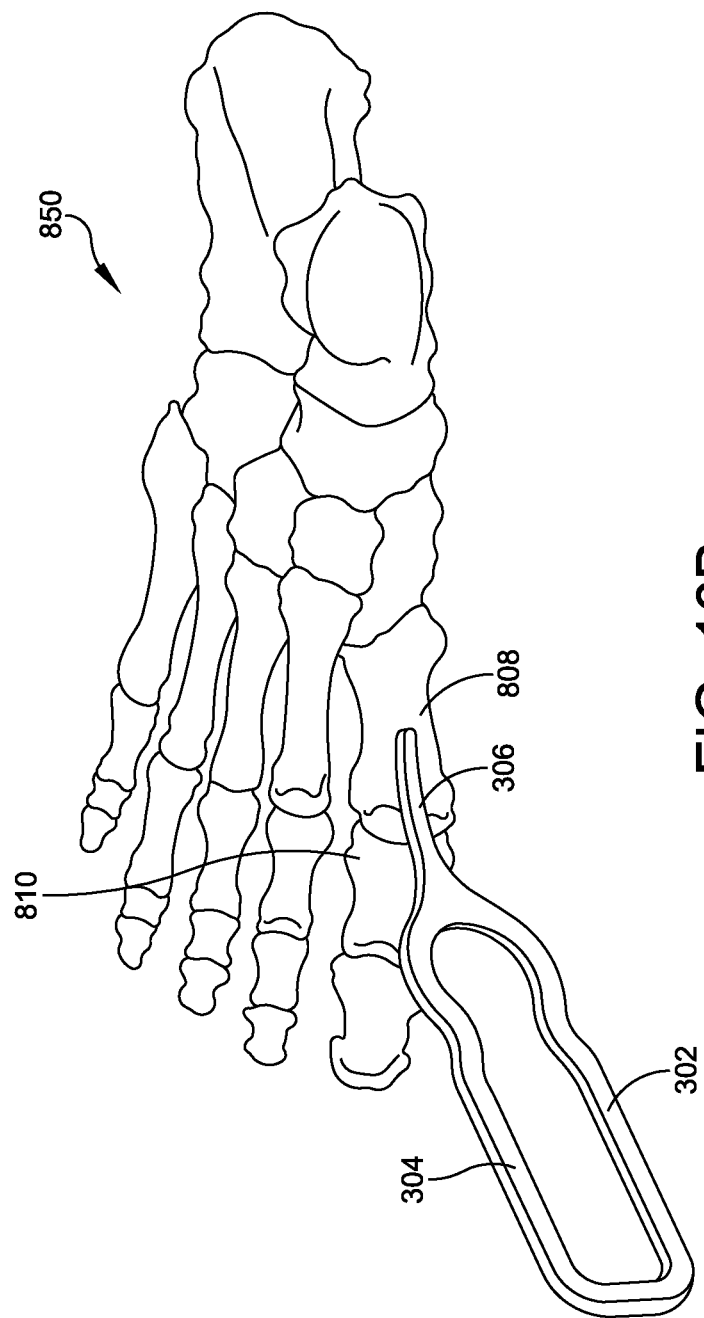

At step 704, a portion of the metatarsal, such as the metatarsal head, is displaced from an initial position, as shown in FIG. 15B. In some embodiments, the displacement of the metatarsal head is achieved by a displacement elevator 302 as shown and described herein. As shown in FIGS. 16A-16B, a displacement tip 306 of an elevator 302 can be positioned near a metatarsal 808 to displace a portion of the metatarsal. The body 304 of the elevator 302 is rotated such that the displacement tip 306 displaces a first portion 810 from a second portion of the metatarsus 808 to form an osteotomy. In some embodiments, a portion of the body 304 is sized and configured to maintain a section of the metatarsus 808, 810 in a fixed position after formation of the osteotomy. In some embodiments, the body 304 includes one or more cavities 312, 314 sized and configured to receive a portion of the patient's anatomy, such as, for example, one or more phalanges.

Figure 17A:
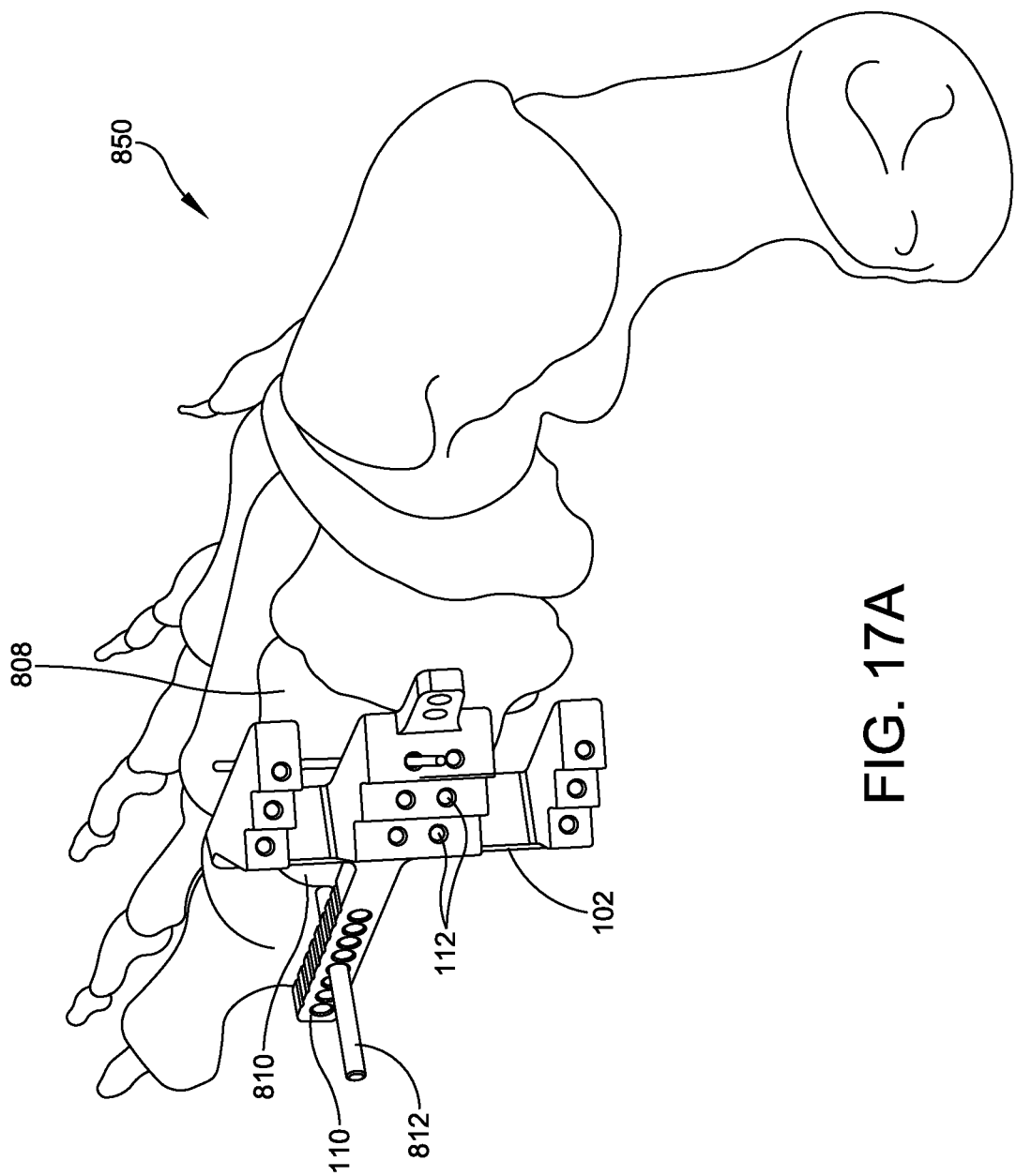
FIGS. 17A-17D illustrate one embodiment a step of inserting one or more k-wires into a metatarsus using a targeting guide during the method of FIG. 14, in accordance with the present disclosure.
Figure 17B:
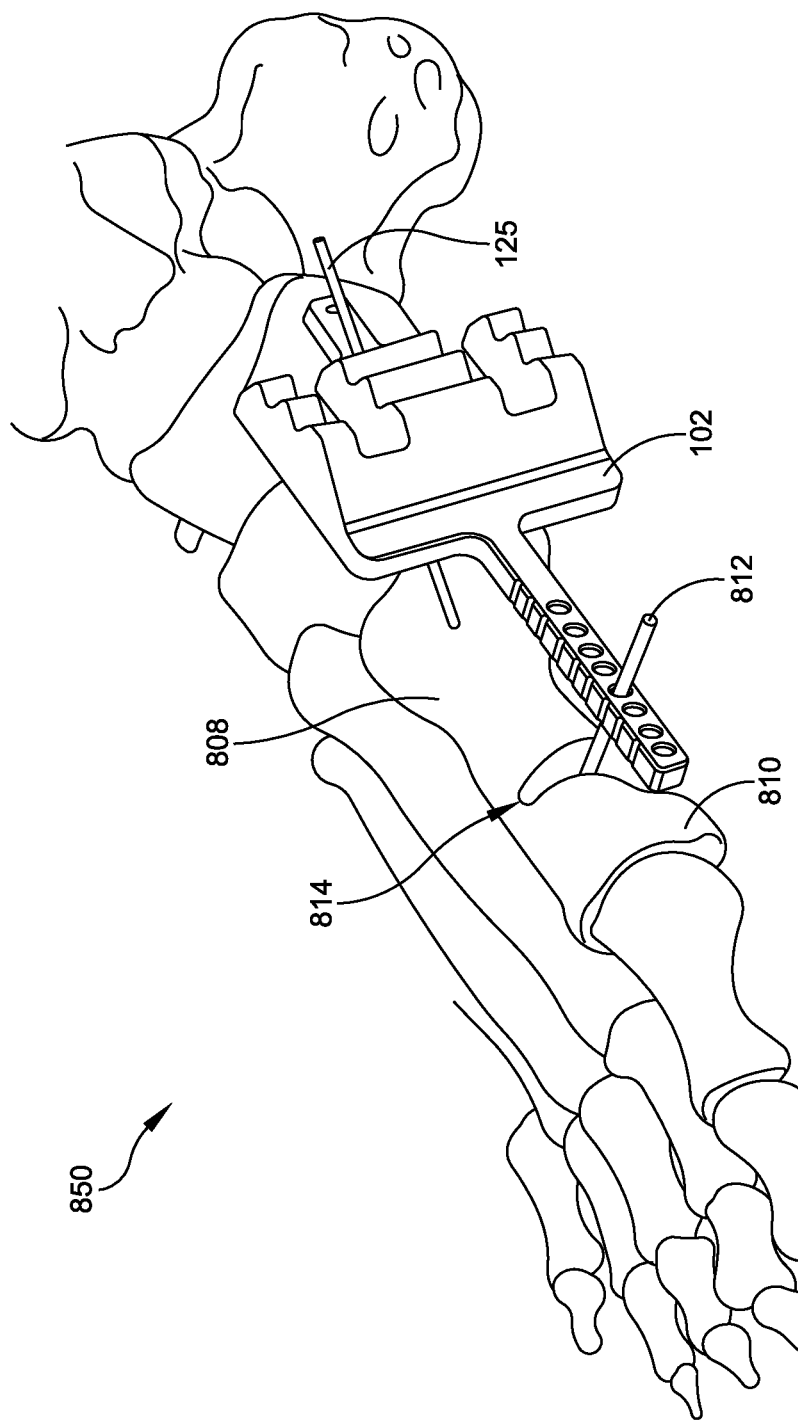
Figure 17C:
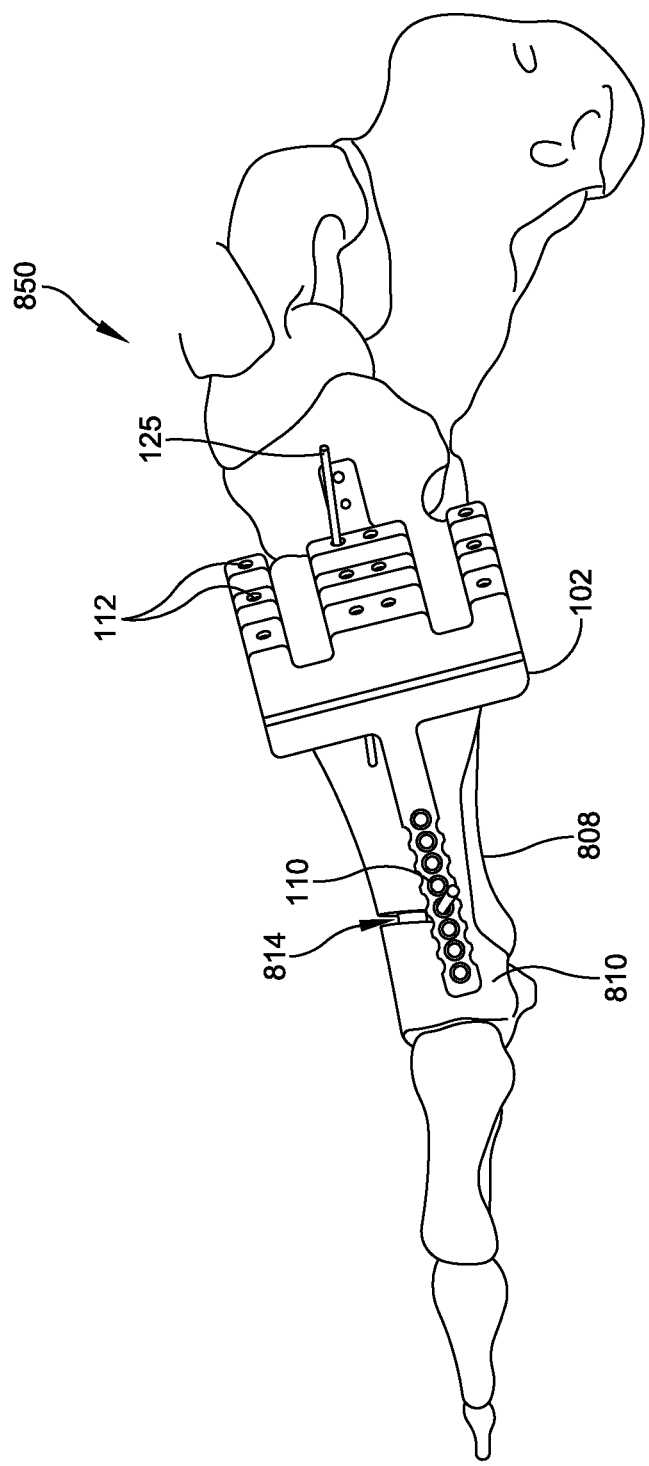
Figure 17D:
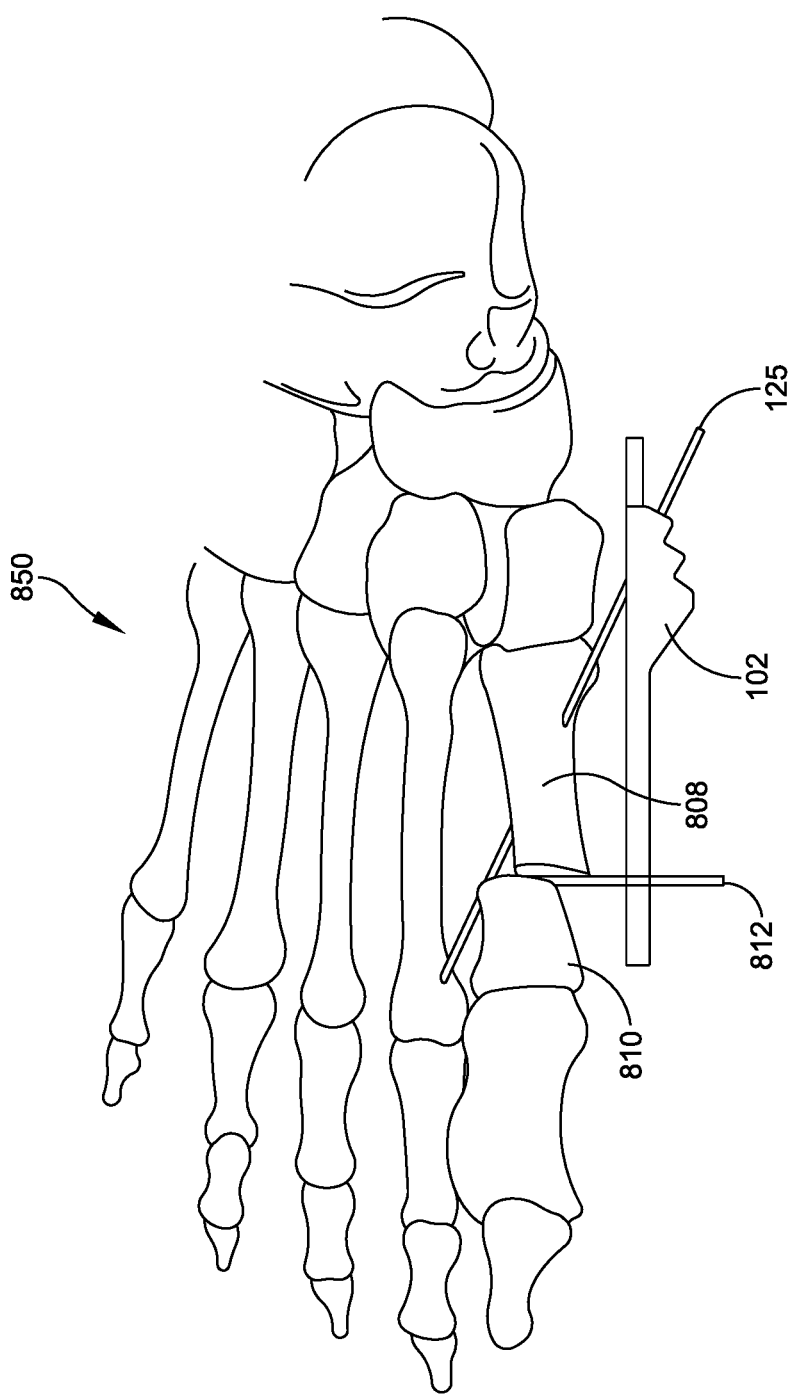

At step 706, one or more k-wires 125 are inserted into a portion of the patient's anatomy, such as one or more phalanges 806a, 806b and/or metatarsals 808. The k-wires 125 can be inserted through a targeting guide, such as the targeting guide 102 illustrated above. FIGS. 17A-17C illustrate insertion of one or more k-wires through a target guide 102. A targeting guide 102 can placed against an outer surface of a patient's foot 850 near the metatarsus 808. The targeting guide 102 is slidably coupled to a burr 812 previously inserted into the metatarsus 808. In some embodiments, the burr 812 is inserted perpendicular to a longitudinal axis of the metatarsus 808.

The targeting guide 102 is inserted over the burr 812 to position a plurality of k-wire guide holes 112 next to the metatarsal 808. As shown in FIGS. 14B-14D, one or more k-wires are inserted into the patient, for example, into the metatarsus 808 through the k-wire guide holes 112. The k-wire guide holes 112 guide the k-wires 125 to a predetermined implantation position within the patient's toe. For example, in some embodiments, the k-wires 125 are implanted through the guide holes 112 to one or more positions corresponding to a chevron osteotomy.

At step 708, after the k-wires 125 are implanted, the targeting guide 102 can be removed from the surgical site 802. The k-wires 125 can be inserted from a dorsal (proximal fragment) to planter (head fragment), for example, utilizing a long tail/plantar limb of the chevron and/or can be inserted from a dorsomedial (proximal fragment) to planter lateral (head fragment). In some embodiments, a k-wire 125 is inserted through one or more cortices of the proximal fragment prior to entry into the metaphysis of the head fragment. In some embodiments, the burr 812 is removed from the metatarsal and the targeting guide 102 is slidably removed over the k-wires 125. In some embodiments, a cut is made in the metatarsus 808 to facilitate removal of the targeting guide 102 and burr 812. The cut may be formed by, for example, the burr 812 and/or any other suitable cutting instrument.

At step 710, the osteotomy is fixed using one or more fixation devices 820. For example, in some embodiments, one or more screws may be inserted through a first portion 808 into a second portion 810 to fix the osteotomy. In some embodiments, the fixation devices include cannulated screws inserted from the second portion 808 to a first portion 810 of the metatarsus 808. In other embodiments, one or more additional percutaneous k-wires 125 are inserted to permanently fix the osteotomy.

In some embodiments, insertion of one or more fixation devices 820 is facilitated by a surgical guide, such as the surgical guides 600*a*, 600*b* described above. In some embodiments, the surgical guide 600*a*, 600*b* is coupled to a k-wire 125 previously inserted at a surgical site 800. The k-wire 125 can be coupled to the surgical guide 600*a*, 600*b* by sliding the k-wire 125 through one or more holes and/or slots defined by the surgical guide 600*a*, 600*b*. For example, in some embodiments, the surgical guide 600*a* is positioned by sliding a k-wire 125 through a first hole 610 defined by a first arm 608 and a slot 614 defined by an alignment body 612.

Figure 15F:
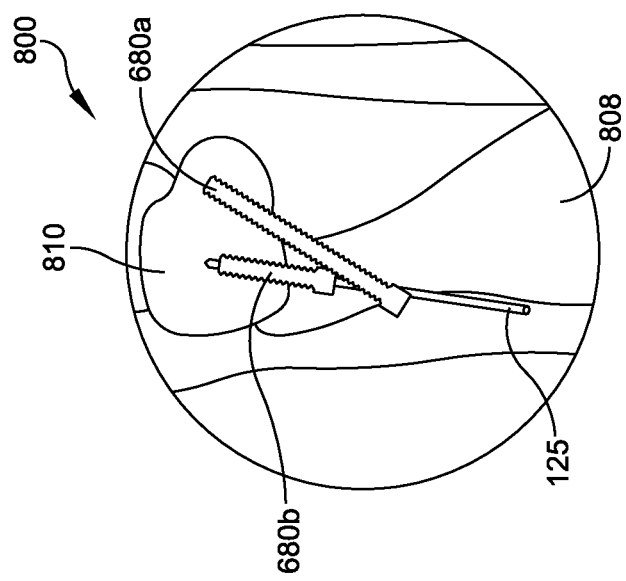
Figure 15D:
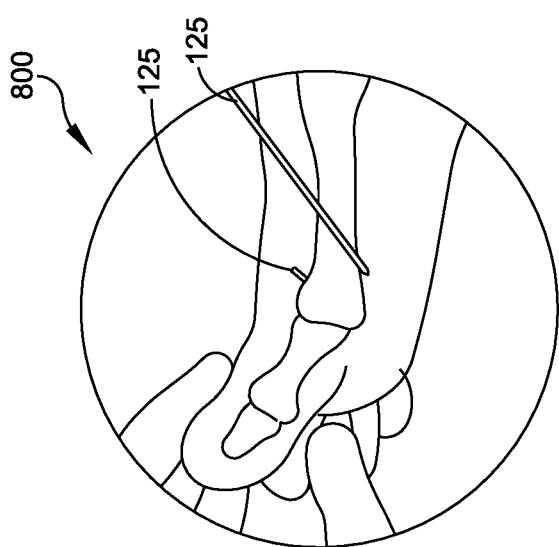
Figure 15G:
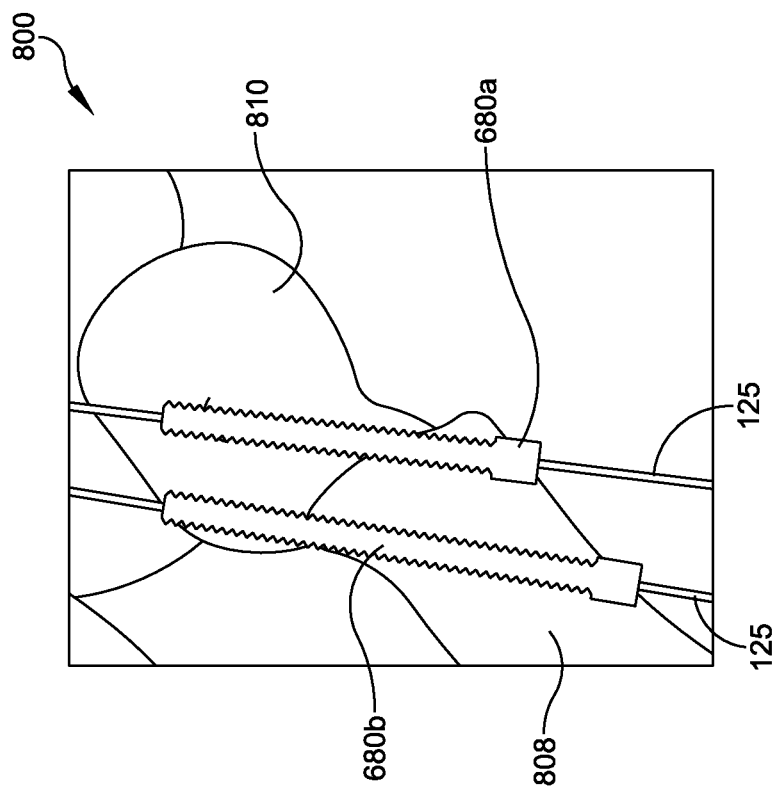

One or more fasteners 680*a*, 680*b* can be inserted through one or more fastener holes 626*a*, 626*b* 674*a*, 674*b* defined in a portion of the surgical guide 600*a*, 600*b*. For example, in some embodiments, a first fastener 680*a* and a second fastener 680*b* are inserted through first and second fastener holes 626*a*, 626*b* formed in a second arm 620 of the surgical guide 600*a*. A first fastener 680*a* can be inserted at an angle with respect to a second fastener 680*b* (as shown in FIG. 15F) and/or can be inserted parallel to the second fastener 680*b* (as shown in FIG. 15G). The fasteners 680*a*, 680*b* maintain the osteotomy in a fixed position during bone healing.

In various embodiments, a targeting guide is disclosed. The targeting guide includes a handle extending substantially along a longitudinal axis. The longitudinal handle defines one or more burr holes extending from a first side of the handle to a second side of the handle. A head is coupled to a distal end of the longitudinal handle. The head defines a plurality of guide holes sized and configured to receive a k-wire therethrough.

In some embodiments, a distal surface of the head comprises a stepped surface including a plurality of offset surfaces. Each of the plurality of offset surfaces can define a distal opening of at least one of the plurality of guide holes.

In some embodiments, a first set of the plurality of guide holes extends through the head at a first angle and a second set of the plurality of guide holes extend through the head at a second angle. The one or more burr holes can extend through a proximal portion of the handle.

In some embodiments, the head defines a cutout extending from the distal surface towards the proximal surface of the head. The cutout is sized and configured to receive a bone therein. The head can include a first tine, a second tine, and a third tine. The first tine is separated from the second tine by a first channel and the second tine is separated from the third tine by a second channel. Each of the first, second, and third tine can define at least one of the plurality of guide holes. In some embodiments, a rectangular anchoring section extends from a distal end of the second tine.

In some embodiments, a rotatable joint couples the handle to the head such that the head is rotatable with respect to the handle.

In various embodiments, an elevator is disclosed. The elevator includes a body defining a first inner cavity sized and configured to receive at least one bone therein and a displacement tip extending from a distal portion of the body. The displacement tip includes a predetermined radius of curvature and is sized and configured to be inserted between a first bone and a second bone. The body can include a closed neck defining a flex point of the body. The body and the closed neck can define the first inner cavity and a second inner cavity. In some embodiments, the body defines an open proximal end.

In various embodiments, a method of forming an osteotomy in a bone is disclosed. The method includes inserting a burr at a surgical site and positioning a targeting guide adjacent to an outer surface of a surgical site. The targeting guide comprises a handle extending substantially along a longitudinal axis. The handle defines at least one burr hole extending from a first side of the handle to a second side of the handle. The targeting guide is slidably coupled to the burr by inserting the burr into the burr hole. One or more k-wires are inserted into at least one bone at the surgical site. The one or more k-wires are inserted through a plurality of guide holes formed in a head of the targeting guide. The targeting guide and the burr are removed from the surgical site after inserting the k-wires.

In some embodiments, a bone at the surgical site is cut prior to coupling the targeting guide to the burr. The cut separates the bone into a first bone portion and a second bone portion.

In some embodiments, the method further includes inserting an elevator between the first bone portion and the second bone portion at the surgical site. The elevator comprises a body defining a first inner cavity sized and configured to receive at least one bone therein and a displacement tip extending from a distal portion of the body. The displacement tip includes a predetermined radius of curvature and is sized and configured to be inserted between the first bone portion and the second bone portion. An osteotomy is formed between the first bone portion and the second bone portion using the elevator. The osteotomy can be a chevron osteotomy.

In some embodiments, the step of inserting one or more k-wires into the at least one bone includes inserting a first k-wire through a first guide hole in the head and inserting a second k-wire through a second guide hole in the head. The first guide hole is defined by a first tine extending from a base of the head and the second guide hole is defined by a second tine extending from the base of the head. In some embodiments, the bone comprises a metatarsal.

In some embodiments, a surgical guide is disclosed. The surgical guide includes a body including central section extending from a first end to a second end and defining a first slot between the first end and the second end and a first arm extending from the first end of the central section and defining a first hole. An alignment body is slidably received within the first slot defined by the central section of the body. A locking mechanism is coupled to a first end of the alignment body. The locking mechanism is configured to lock the alignment body at a location along a length of the first slot defined by the central section of the body.

In some embodiments, the alignment body defines a second slot that inwardly extends from a second end of the alignment body. The first hole and the second slot are configured to receive an elongate surgical instrument therein. A second arm can extend from the second end of the central section.

In some embodiments, the locking mechanism includes a thumb screw. In some embodiments, the locking mechanism includes a wing nut.

In some embodiments, the first hole defined by the first arm aligns with the second slot defined by the alignment body. The alignment body can be configured to move along the length of the first slot defined by the body and to move transversely relative to a longitudinal axis defined by the first slot.

In some embodiments, the second arm defines a pair of parallel holes adjacent to an end thereof. The first arm can extend perpendicularly from the central section and the second arm can extend from the central section at an angle between zero and ninety degrees.

In some embodiments, the first slot extends through a first side and a second side of the central section. The central section can define a second slot that extends through a third side and a fourth side of the central section of the body. The first hole can extend through the first arm in a direction that is perpendicular to a longitudinal direction of the central section.

In some embodiments, the alignment body defines a second hole that extends through the alignment body in a first direction and defines a third hole that extends through the alignment body in a second direction. The first direction can be parallel to the second direction.

In some embodiments, the alignment body is configured pivot about and axis that is oriented perpendicularly with respect to a longitudinal direction of the central section.

In some embodiments, the first arm is configured to rotate about a longitudinal axis defined by the central section of the body and is configured to slide in directions that are perpendicular to a longitudinal axis defined by the central section of the body.

In various embodiments is disclosed. The method includes inserting a guide wire into a shaft of a metatarsal without inserting the guide wire into a head of the metatarsal, coupling an alignment guide to the guide wire, displacing the head of the metatarsal using the alignment guide, inserting a first screw into a first hole defined by the alignment guide, and inserting a second screw into a second hole defined by the alignment guide. The first hole can define a first axis that is parallel to a second axis defined by the second hole.

In some embodiments, the first and second holes are defined by an arm extending from a central section of the alignment guide. The first and second holes can be defined by an alignment body that is slidably received within a slot defined by a central section of the alignment guide.

In various embodiments, a method is disclosed. The method includes inserting a guide wire in a medial-to-lateral direction through a first head of a first metatarsal and into a second head of a second metatarsal, coupling an alignment guide to the guide wire, inserting a first screw into a first hole defined by the alignment guide, and inserting a second screw into a second hole defined by the alignment guide. The first hole can define a first axis that is parallel to a second axis defined by the second hole.

In some embodiments, the first and second holes are defined by an arm extending from a central section of the alignment guide. In some embodiments, the first and second holes are defined by an alignment body that is slidably received within a slot defined by a central section of the alignment guide.

Although the subject matter has been described in terms of exemplary embodiments, it is not limited thereto. Rather, the appended claims should be construed broadly, to include other variants and embodiments, which may be made by those skilled in the art.

What is claimed is:

1. A system comprising:
a targeting guide comprising a first portion defining a plurality of apertures and a first passageway, the plurality of apertures being disposed adjacent to a first end of the first portion, each aperture of the plurality of apertures sized and configured to guide at least one first elongate surgical instrument along a respective trajectory, the first passageway extending along at least a portion of a length of the first portion;
a second portion configured to move relative to the first portion along a path defined by the first passageway, the second portion including at least one surface configured to abut a first bone when the targeting guide is placed adjacent to the first bone and a second bone, the second portion defining an opening sized and configured to receive a second elongate surgical instrument;
further comprising a first cannulated screw sized and configured to be positioned over the at least one first elongate surgical instrument; and
a releasable lock configured to retain the second portion at a variety of positions selected along the first passageway defined by the first portion.

2. The system of claim 1, wherein the releasable lock includes a thumb screw.

3. The system of claim 1, wherein the second portion is configured to move transversely relative to a longitudinal axis defined by the first passageway.

4. The system of claim 1, wherein the second portion has an enlargement that includes the at least one surface configured to abut at least one of the first bone and the second bone.

5. The system of claim 1, further comprising a second cannulated screw sized and configured to be positioned over the at least one first elongate surgical instrument.

6. The system of claim 5, wherein the plurality of apertures are arranged parallel to each other.

7. The system of claim 5, wherein at least one of the plurality of apertures is disposed in a non-parallel relationship to another one of the plurality of apertures.

8. A method, comprising:
segmenting a bone into a first bone segment and a second bone segment;

moving the first bone segment relative to the second bone segment such that the first bone segment and the second bone segment are spaced-apart;

adjusting a position of a second body portion of a targeting guide relative to a first body portion of the targeting guide by moving the second body portion along a path defined by a slot defined by the first body portion of the targeting guide while the targeting guide is disposed adjacent to the bone such that the first body portion of the targeting guide is disposed adjacent to the second bone segment and the second body portion of the targeting guide abuts the second bone segment;

locking the position of the second body portion at a location along the path defined by the slot of the first body portion;

inserting a k-wire into a first aperture of a plurality of apertures defined by the first body portion of the targeting guide such that the k-wire extends through the second bone segment and into the first bone segment; and inserting a first cannulated screw over the k-wire such that the first cannulated screw is disposed at least partially within the first bone segment and the second bone segment.

9. The method of claim 8, further comprising removing the targeting guide from its engagement with the k-wire prior to inserting the first cannulated screw over the k-wire.

10. The method of claim 8, further comprising inserting a second k-wire into a second aperture of the plurality of apertures defined by the first body portion such that the first k-wire extends through the second bone segment and into the first bone segment; and inserting a second cannulated screw over the second k-wire such that the second cannulated screw is disposed at least partially within the first bone segment and the second bone segment.

11. The method of claim 8, wherein locking the position of the second body portion relative to the first body portion includes rotating at least a portion of a locking mechanism.

12. The method of claim 11, wherein the locking includes manipulation of at least one of a thumb screw or a wing nut.

13. A system, comprising:

a targeting guide including:

a first portion extending from a first end to a second end, the first end of the first portion defining a plurality of apertures each sized and configured to a k-wire, the first portion defining a slot located between the first end and the second end of the first portion;

a second portion coupled to the first portion such that the first portion and the second portion are arranged so as to move relative to one another in a path defined by the slot, the second portion including at least one surface configured to abut a first bone when the targeting guide is placed adjacent to the first bone and a second bone, the second portion defining an opening sized and configured to receive a second k-wire;

further comprising a first cannulated screw sized and configured to be disposed at least partially within the first bone and the second bone, the first cannulated screw defining a first cannulation sized and configured to receive the k-wire; and a releasable lock including a rotating portion, the releasable lock configured to prevent relative movement between the first portion and the second portion.

14. The system of claim 13, wherein the plurality of apertures defined by the first portion are arranged parallel to each other.

15. The system of claim 14, further comprising a second cannulated screw sized and configured to be disposed at least partially within the first bone and the second bone, the second cannulated screw defining a second cannulation sized and configured to receive the second k-wire.

* * * * *